US010517608B2

(12) United States Patent
Jenkins et al.

(10) Patent No.: US 10,517,608 B2
(45) Date of Patent: Dec. 31, 2019

(54) APPARATUS TO FORM OPENING IN ETHMOID BULLA AND IRRIGATE ETHMOID SINUS CAVITY

(71) Applicant: Acclarent, Inc., Menlo Park, CA (US)

(72) Inventors: Thomas R. Jenkins, Alameda, CA (US); Meera L. Sankaran, Cupertino, CA (US); Alfredo R. Cantu, Pleasanton, CA (US); Rohit Girotra, Mountain View, CA (US)

(73) Assignee: Acclarent, Inc., Irvine, CA (US)

( * ) Notice: Subject to any disclaimer, the term of this patent is extended or adjusted under 35 U.S.C. 154(b) by 684 days.

(21) Appl. No.: 14/837,594

(22) Filed: Aug. 27, 2015

(65) Prior Publication Data

US 2017/0056043 A1    Mar. 2, 2017

(51) Int. Cl.
*A61B 17/3209* (2006.01)
*A61B 17/3205* (2006.01)
(Continued)

(52) U.S. Cl.
CPC ...... *A61B 17/1615* (2013.01); *A61B 17/1604* (2013.01); *A61B 17/1688* (2013.01); *A61B 17/24* (2013.01); *A61B 17/1633* (2013.01); *A61B 17/32053* (2013.01); *A61B 2017/3425* (2013.01); *A61B 2017/3458* (2013.01); *A61B 2217/005* (2013.01); *A61B 2217/007* (2013.01)

(58) Field of Classification Search
CPC ............ A61B 17/1604; A61B 17/1615; A61B 17/1633; A61B 17/32053; A61B 2017/320024; A61B 2017/320791; A61B 10/0266; A61B 17/320758; A61B 2017/00685; A61B 2017/320775

USPC ....................................... 606/180; 604/19–22
See application file for complete search history.

(56) References Cited

U.S. PATENT DOCUMENTS 4,790,312 A * 12/1988 Capuano, Sr. .............................
.................................................. A61B 17/320016
606/171
4,790,812 A * 12/1988 Hawkins, Jr. ........ A61B 17/221
604/22

(Continued)

OTHER PUBLICATIONS

International Search Report and Written Opinon dated Nov. 18, 2016 for Application No. PCT/US2016/046555, 12 pgs.

(Continued)

*Primary Examiner* — Kathleen S Holwerda
(74) *Attorney, Agent, or Firm* — Frost Brown Todd LLC

(57) ABSTRACT

An instrument for treating a sinus cavity includes a cutter member, a rotatable member, and a fluid passage. The cutter member has a lumen extending therealong, and the rotatable member is received within the lumen. The rotatable member has a helical blade projecting from a distal end portion. The cutter member is configured to translate relative to the rotatable member. Thereby, the cutter member and the rotatable blade are configured to form an opening into the sinus cavity. The fluid passage extends through the cutter member from an inlet to an outlet. The outlet is positioned proximal to the helical blade such that the outlet is configured to fluidly communicate with the sinus cavity. The inlet is configured to receive at least one of a fluid and a vacuum in order to communicate the respective fluid or vacuum to the outlet for irrigating or suctioning the sinus cavity.

17 Claims, 40 Drawing Sheets

(51) Int. Cl.
*A61B 17/16* (2006.01)
*A61B 17/24* (2006.01)
*A61B 17/34* (2006.01)

(56) References Cited

U.S. PATENT DOCUMENTS

| | | | | |
|---|---|---|---|---|
| 5,007,917 | A * | 4/1991 | Evans | A61B 17/32002 604/22 |
| 5,047,040 | A * | 9/1991 | Simpson | A61B 17/3207 604/22 |
| 5,405,348 | A | 4/1995 | Anspach, Jr. et al. | |
| 6,551,255 | B2 * | 4/2003 | Van Bladel | A61B 10/0266 600/584 |
| 7,806,871 | B2 * | 10/2010 | Li | A61B 17/32002 604/164.06 |
| 8,317,727 | B2 * | 11/2012 | Peliks | A61B 10/0266 600/562 |
| 8,864,774 | B2 | 10/2014 | Liu et al. | |
| 9,155,492 | B2 | 10/2015 | Jenkins et al. | |
| 9,155,555 | B2 | 10/2015 | O'Brien, II | |
| 9,629,684 | B2 | 4/2017 | Jenkins et al. | |
| 9,724,073 | B2 * | 8/2017 | Hathaway | A61B 10/0275 |
| 2006/0253069 | A1 | 11/2006 | Li et al. | |
| 2009/0270894 | A1 * | 10/2009 | Rubin | A61B 17/32002 606/170 |
| 2010/0030031 | A1 | 2/2010 | Goldfarb et al. | |
| 2011/0004057 | A1 | 1/2011 | Goldfarb et al. | |

OTHER PUBLICATIONS

European Communication dated Aug. 7, 2019 for Application No. 16754610.0, 5 pages.

* cited by examiner

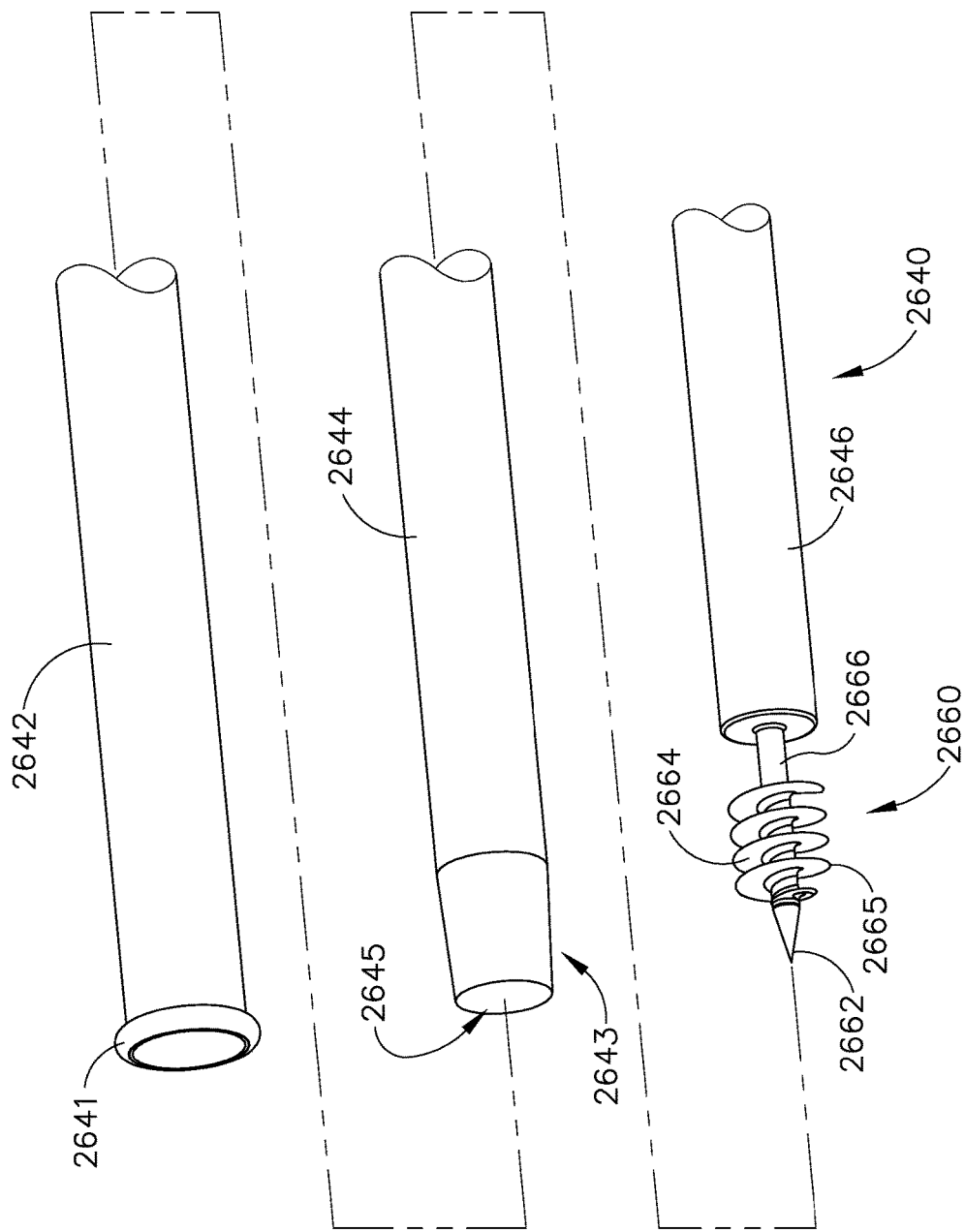

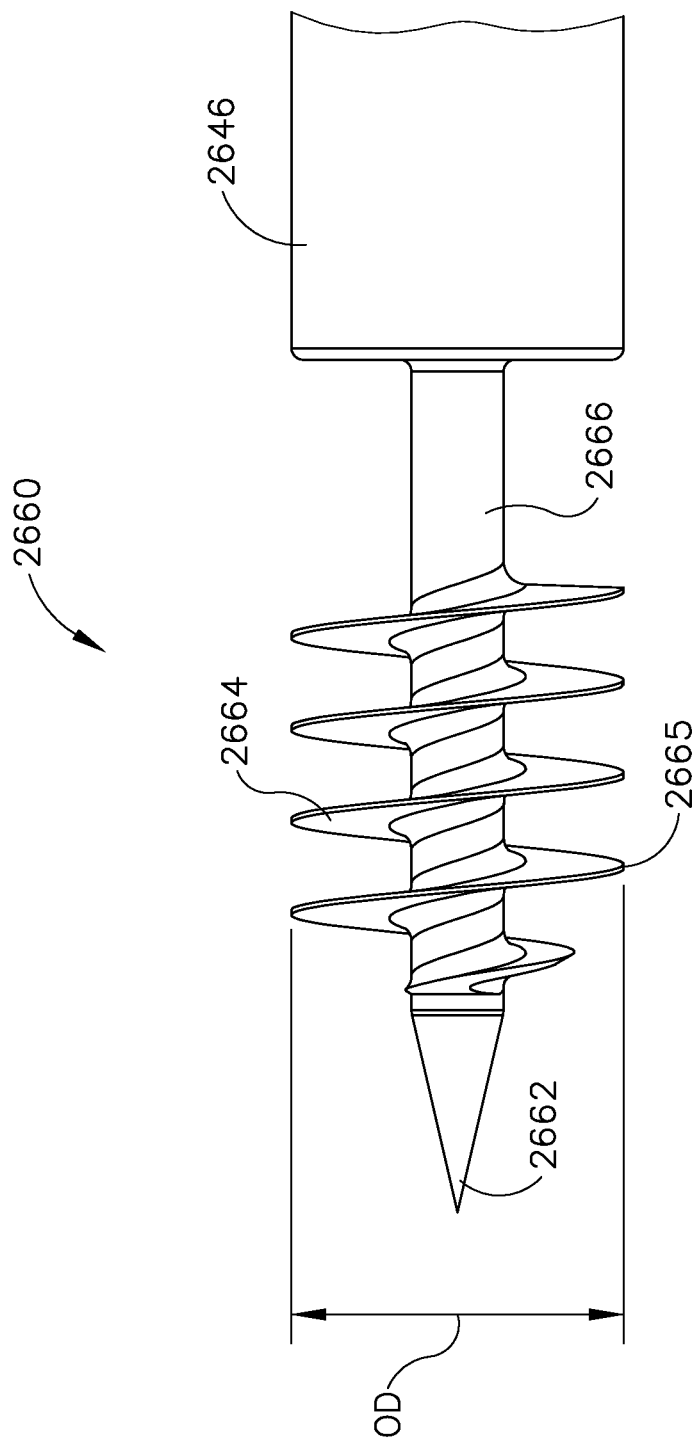

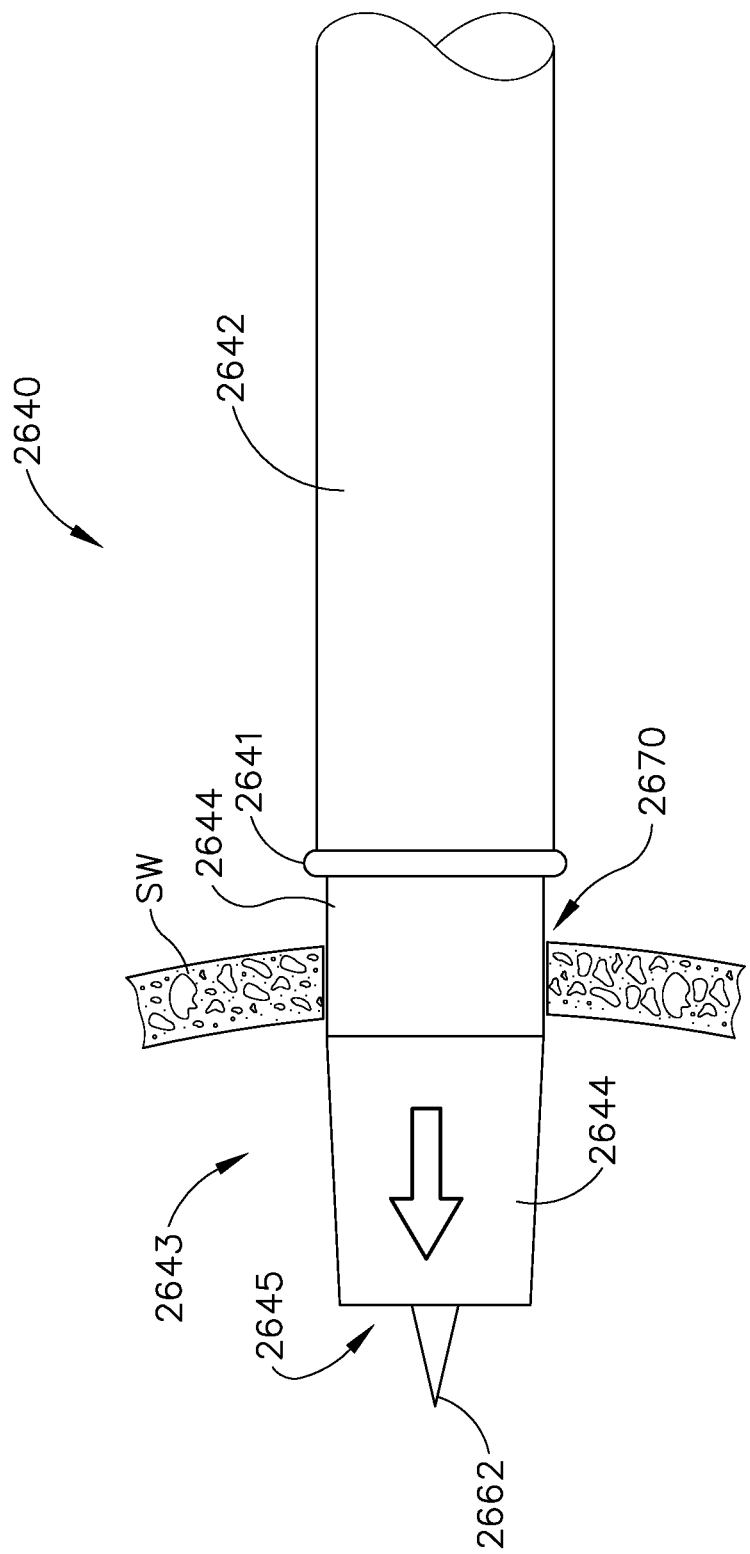

ated Sep. 18, 2014, issued as U.S.
APPARATUS TO FORM OPENING IN ETHMOID BULLA AND IRRIGATE ETHMOID SINUS CAVITY

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif. Another system that may be used to perform such procedures may be provided in accordance with the teachings of U.S. Pub. No. 2014/0277043, entitled "Apparatus and Method for Treatment of Ethmoid Sinusitis," published Sep. 18, 2014, issued as U.S. Pat. No. 9,629,684 on Apr. 25, 2017, the disclosure of which is incorporated by reference herein.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

While several instruments and procedures have been made and used for treatment of anatomical passageways in a patient, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 7 depicts an exploded perspective view of a shaft assembly of the instrument of FIG. 3;

FIG. 8 depicts a detailed side elevational view of an exemplary auger of the shaft assembly of FIG. 7;

FIG. 9D depicts a side elevational view of the shaft assembly of FIG. 7 in the second longitudinal position, with the outer sheath still in the second longitudinal position, and with the cutter moved to a second longitudinal position;

Figure 1:
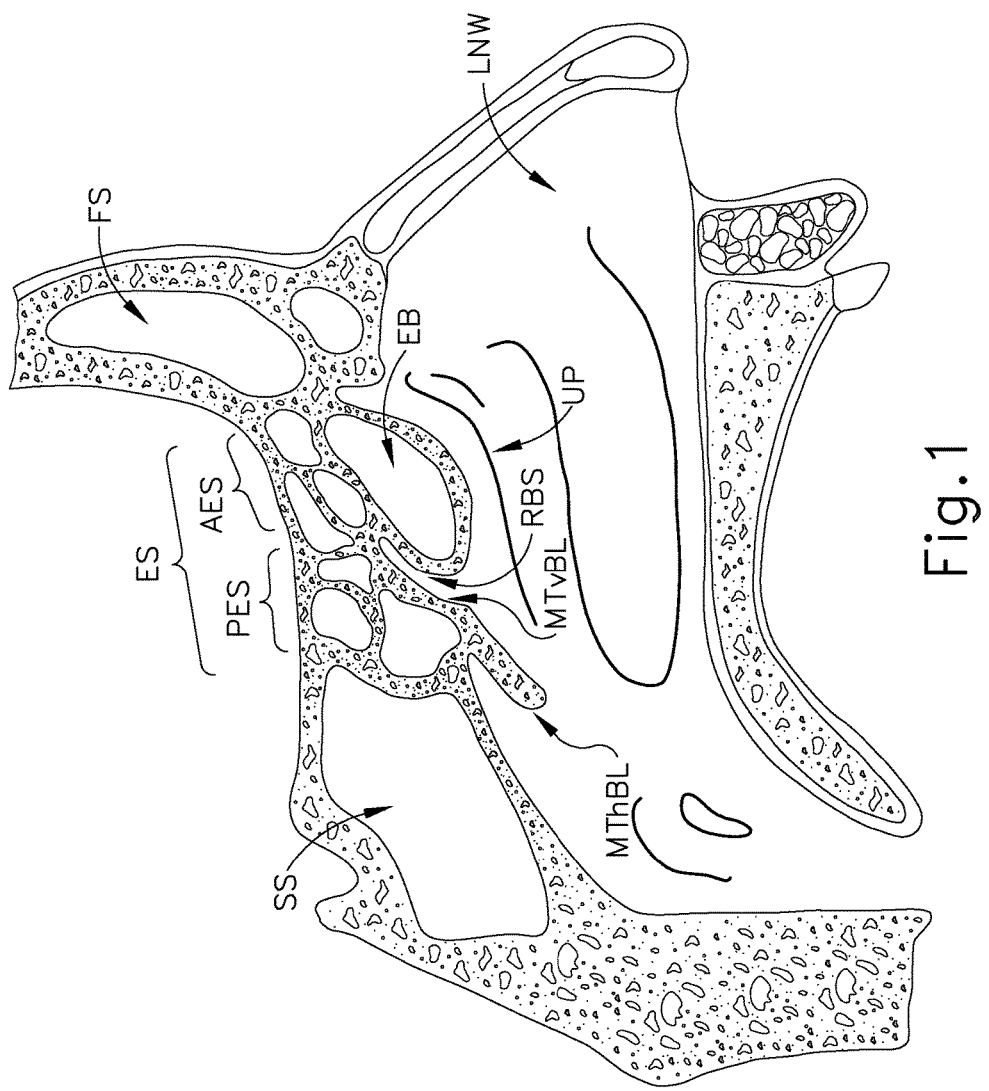
FIG. 1 depicts a left sagittal cross-sectional view of a portion of a human head, showing paranasal sinus structures.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY PORT FOR ETHMOID SINUS

FIG. 1 shows a left sagittal cross-sectional view of a portion of a human head, which includes a sphenoid sinus (SS), ethmoid sinus (ES), frontal sinus (FS), middle turbinate horizontal basal lamella (MThBL), middle turbinate vertical basal lamella (MTvBL), uncinate process (UP), and lateral nasal wall (LNW). The ethmoid sinus (ES) comprises a set of sinus cells that may be categorized as anterior ethmoid sinus (AES) cells and posterior ethmoid sinus (PES) cells. The ethmoid bulla (EB) is the largest ethmoid sinus (ES) cell, and is generally inferior and anterior to the other cells of the ethmoid sinus (ES). The posterior wall of the ethmoid bulla (EB) and the middle turbinate vertical basal lamella (MTvBL) together define a retrobullar space (RBS). It should be understood that anatomical variation in the human is such that this retrobullar space (RBS) may or may not be present in a given individual.

The ethmoid sinus (ES) includes ostia (not shown) for providing fluid communication to and from the cells of the ethmoid sinus (ES) and the nasal cavity. For instance, ostia may provide fluid paths for cells within the anterior ethmoid sinus (AES), cells within the posterior ethmoid sinus (PES), and the ethmoid bulla (EB). In some instances, suprabullar cells of the ethmoid sinus (ES) drain into the ethmoid bulla (EB). Some suprabullar cells may drain directly into the retrobullar space (RBS). The ethmoid bulla (EB) may itself provide fluid communication with the nasal cavity via one or more ostia, such that the ethmoid bulla (EB) may provide a fluid communication path between the other ethmoid sinus (ES) cells (that drain into the ethmoid bulla (EB)) and the nasal cavity. For instance, the ethmoid bulla (EB) may provide fluid communication through an ostium at the retrobullar space (RBS). The fluid communication paths provided by ostia may allow the entry of air and liquids (e.g., medications); while also allowing drainage of mucus. In some instances, the ostia may become blocked, may become functionally closed due to mucosal thickening, or may otherwise not provide sufficient fluid communication. In addition or in the alternative, the configuration of the retrobullar space (RBS) may impede flow through the ostium of the ethmoid bulla (EB).

The anatomy of the ethmoid sinus (ES) may make it impractical to perform a dilation procedure on ostia of the ethmoid sinus (ES) using dilation catheter system (10) to improve fluid communication within the ethmoid sinus (ES). This may lead some operators to perform an ethmoidectomy, which is an invasive procedure that involves removal of ethmoid sinus (ES) portions (e.g., tissue and bone) using an instrument such as a debriding instrument. This kind of procedure may be somewhat crude an inelegant, resulting in removal of significant amounts of mucosa that might otherwise benefit the patient. Ethmoidectomy procedures may also have risks of inadvertent damage to optic nerves, damage to orbital muscles, damage to olfactory bulbs, damage to other anatomical structures, and even leakage of cerebrospinal fluid. Even in successful ethmoidectomies, the patient may need to return for several follow-up debridements. It may therefore be desirable to improve fluid communication from within the ethmoid sinus (ES) to the nasal cavity without resorting to a procedure like an ethmoidectomy. In some instances, this may involve implantation of a port in one or more cells of the ethmoid sinus (ES). Several merely illustrative examples of such ports are described in greater detail below, while other examples will be apparent to those of ordinary skill in the art in view of the teachings herein.

A. Exemplary Port with Single Wall Deployment

Figure 2A:
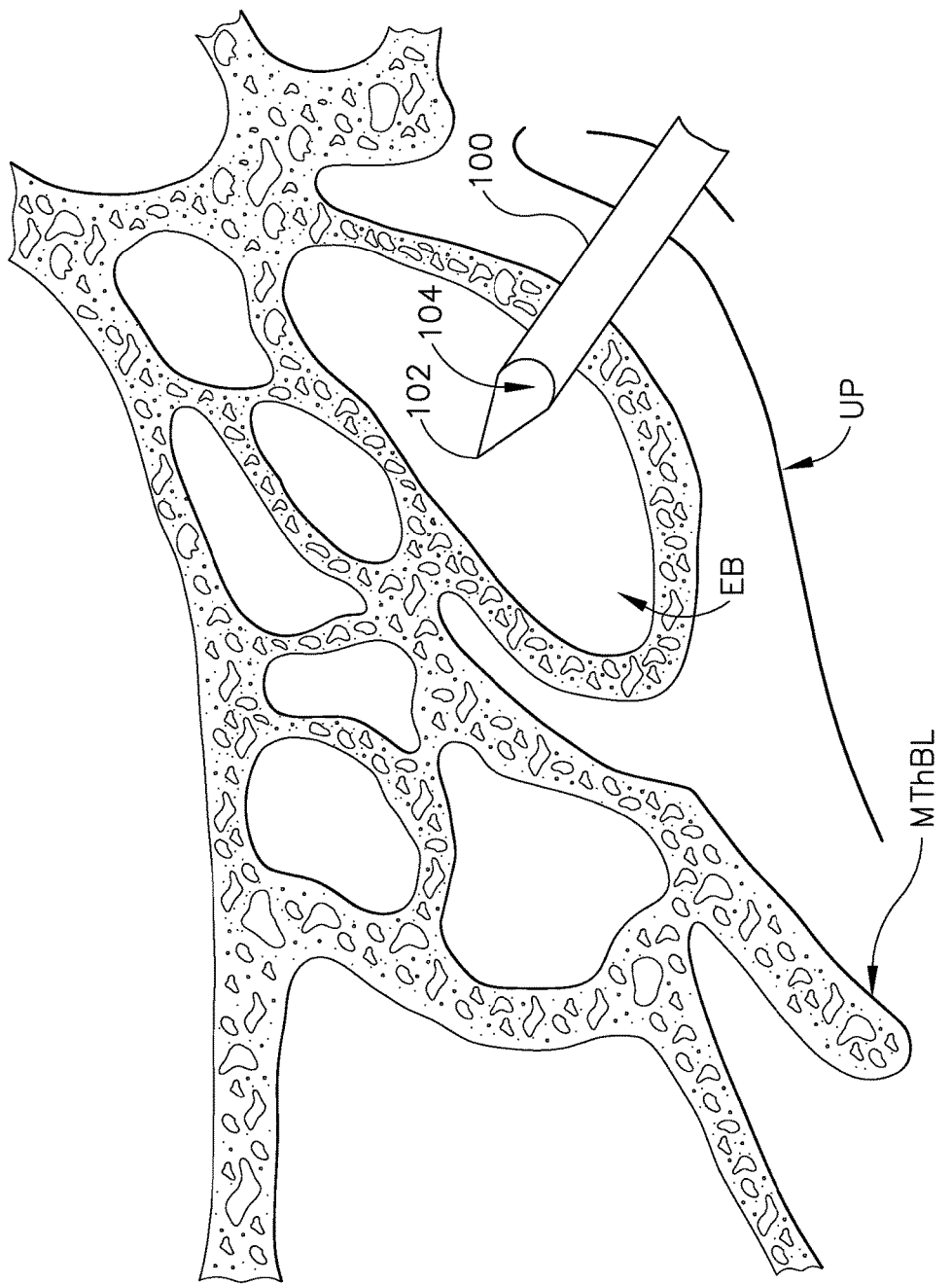
FIG. 2A depicts a left sagittal cross-sectional view of a portion of a human head, with an exemplary port deployment instrument piercing a wall of the ethmoid bulla.

FIG. 2A shows an exemplary instrument (100) that may be used to deploy a port (200) in the ethmoid bulla (EB). Instrument (100) of this example has a piercing tip (102) and an opening (104) proximal to tip (102). In some versions, the outer diameter of instrument (100) is approximately 3 mm, though other dimensions may be used. The mouth of opening (104) lies along a plane that is oblique to the longitudinal axis of instrument (100) in the present example, though it should be understood that opening (100) may instead have other configurations and orientations. Instrument (100) may be introduced through the patient's nose (in this case, the patient's right nostril) and positioned at an anterior/inferior wall of the ethmoid bulla (EB). Instrument (100) may be positioned using visualization from endoscope (60) described above and/or from some other device. A retractable sheath (not shown) may be used to shield tip (102) until instrument (100) reaches the ethmoid bulla (EB).

Once positioned at the ethmoid bulla (EB), instrument (100) may be advanced against the ethmoid bulla (EB) such that tip (102) pierces the wall of the ethmoid bulla (EB), allowing opening (104) to be positioned within the ethmoid bulla (EB) as shown in FIG. 2A. Tip (102) is configured to pierce the wall of the ethmoid bulla (EB) without shattering the wall of the ethmoid bulla (EB). In other words, the wall of the ethmoid bulla (EB) remains intact except for the opening created by instrument (100), with such an opening being approximately the same size as the outer diameter of instrument (100). In some versions, tip (102) is rotated (e.g., by hand, using a torsion spring, etc.) to assist with piercing of the ethmoid bulla (EB). Such rotation may be in one angular direction or may be in opposing angular directions (e.g., in a rocking motion). In addition or in the alternative, tip (102) may be imparted with a reciprocating longitudinal motion. Tip (102) may also have an abrasive surface/edge and/or other features that promote piercing of the ethmoid bulla (EB). Various suitable configurations for tip (102) and methods for piercing the ethmoid bulla (EB) with tip (102) will be apparent to those of ordinary skill in the art in view of the teachings herein.

Figure 2B:
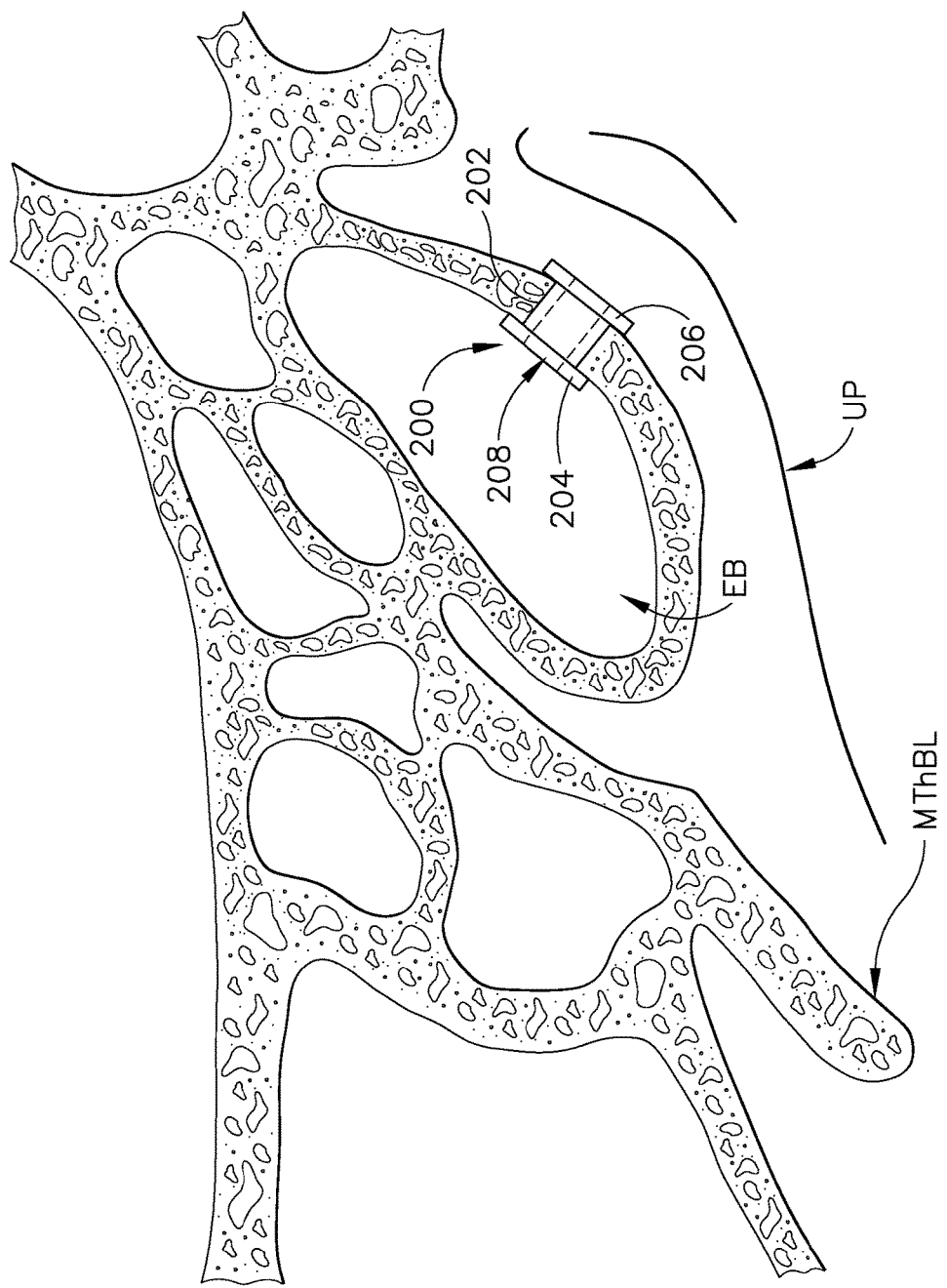
FIG. 2B depicts a left sagittal cross-sectional view of a portion of a human head, with a port disposed in the pierced wall of the ethmoid bulla.

After instrument (100) has pierced the ethmoid bulla (EB), instrument (100) may deploy a port (200) within the opening created in the wall of the ethmoid bulla (EB) by tip (102), as shown in FIG. 2B. By way of example only, instrument (100) may include a translating push-rod or other feature within instrument (100) that is able to drive port (200) out through opening (104). As another merely illustrative example, instrument (100) may be configured and operable in accordance with at least some of the teachings of U.S. Pub. No. 2011/0015645, entitled "Tympanic Membrane Pressure Equalization Tube Delivery System," published Jan. 20, 2011, issued as U.S. Pat. No. 8,864,774 on Oct. 21, 2014, the disclosure of which is incorporated by reference herein. In such versions, port (200) may be generally analogized to the pressure equalization tube deployed in a patient's tympanic membrane. Various other suitable ways in which port (200) may be deployed in the wall of the ethmoid bulla (EB) will be apparent to those of ordinary skill in the art in view of the teachings herein.

Port (200) of the present example comprises a cylindraceous body (202), a first flange (204) at one end of body (202), and a second flange (206) at the other end of body (202). Body (202) is hollow and defines a lumen (208) extending from flange (204) to flange (206). As shown in FIG. 2B, flange (204) is positioned within the interior of the ethmoid bulla (EB) while flange (206) is positioned at the exterior of the ethmoid bulla (EB). Flanges (204, 206) are configured to generally maintain the position of port (200) with respect to the ethmoid bulla (EB). Flanges (204, 206) may be separated from each other by any other suitable distance, such that body (202) may extend to any suitable length. In some versions, only one flange (204, 206) is provided. For instance, flange (206) may be omitted in some versions.

Port (200) may be formed of a resilient material, such that port (200) is compressed while port (200) is within instrument (100); with port (200) resiliently assuming the rivet like shape shown in FIG. 2B as soon as port (200) exits instrument (100). In some other versions, port (200) is formed of a malleable material. In some such versions, instrument (100) includes features that form the rivet like shape of port (200) as port (200) is deployed in the wall of ethmoid bulla (EB). It should also be understood that port (200) may be formed of a bioabsorbable or biodegradable material. In versions where port (200) is formed of a bioabsorbable material, the bioabsorbable material forming port (200) may include one or more therapeutic materials. In some versions where port (200) is formed of a non-bioabsorbable/non-biodegradable material, port (200) may eventually be removed from the patient some time after implantation. Port (200) may also be formed of a material that is configured to wick fluids. By way of example only, port (200) may be formed of semi-flexible, porous polyethylene, with a pore size selected to optimize wicking and with a surface coating/treatment to make port (200) hydrophilic. Various suitable materials that may be used to form port (200) will be apparent to those of ordinary skill in the art in view of the teachings herein.

It should be understood that, once port (200) has been deployed, lumen (208) enables the substantially free communication of air/mucus/etc. into and out of the ethmoid bulla (EB). Port (200) thus serves as a substitute or supplemental ostium for the ethmoid bulla (EB). In some instances, the patient may be instructed to periodically self-administer medications or other fluids within their nose after a port (200) has been implanted. By way of example only, such fluids/medications may include saline, a combination of saline and a surfactant, an anti-inflammatory (e.g., mometasone, etc.), an antibiotic, an anti-fungal, and/or various other kinds of fluids/medications, including combinations thereof. Lumen (208) may provide a substantially clear path for such fluids/medications to reach the mucosa within the ethmoid bulla (EB), in addition to providing a vent/drainage path for the ethmoid bulla (EB). In other words, the presence of port (200) may provide substantially greater communication of the administered fluids/medications to the ethmoid bulla (EB) than the communication that would be provided in the absence of port (200). In some variations, a sleeve (not shown) extends from flange (206) and is in fluid communication with lumen (208). Such a sleeve may be directly coupled with a fluid delivery device and/or a suction device to actively deliver fluid or suction to the ethmoid bulla (EB) via port (200). In addition or in the alternative, such a sleeve may provide a wicking function similar to the various wicks described in greater detail below.

B. Exemplary Instrument with Helical Auger and Retractable Sheath

Figure 3:
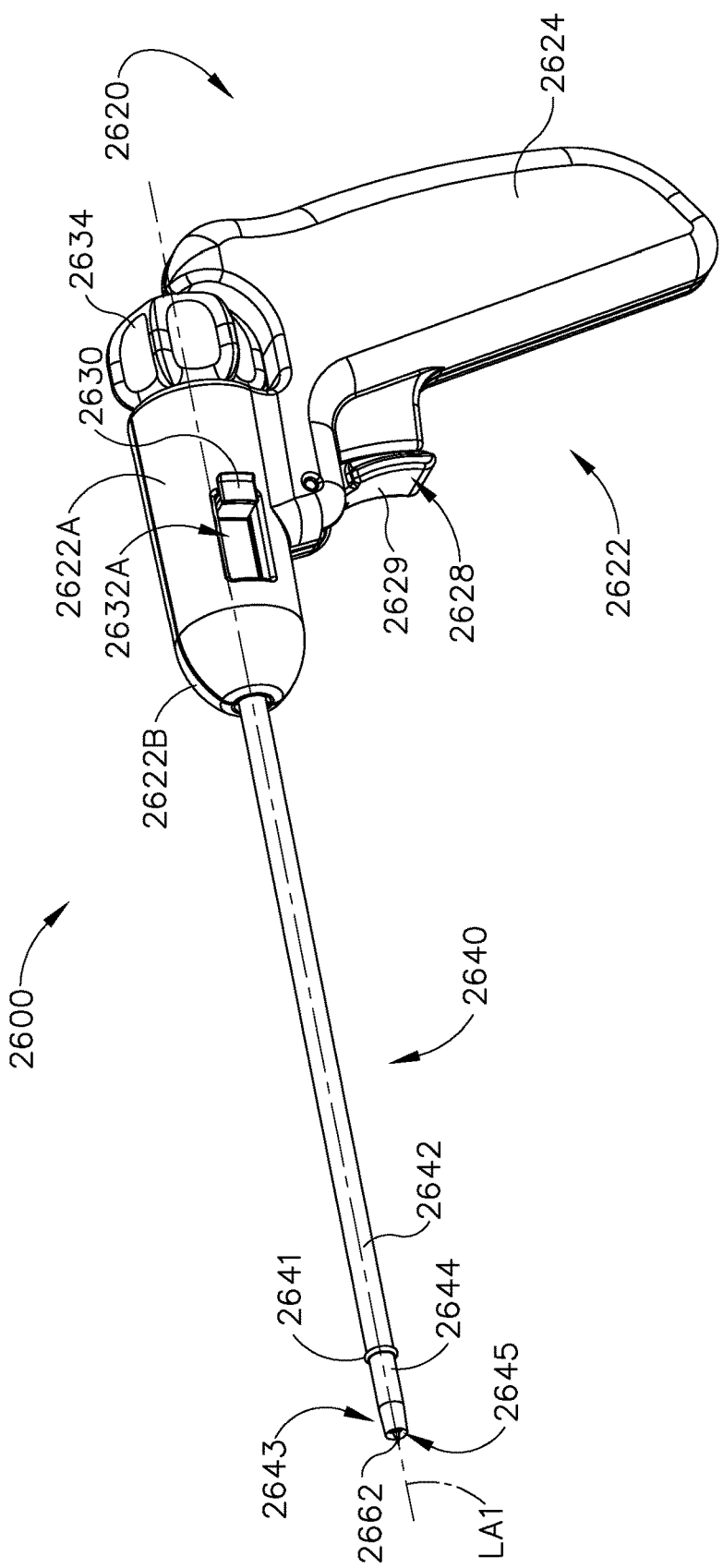
FIG. 3 depicts a perspective view of an exemplary sinus wall piercing instrument.
Figure 4:
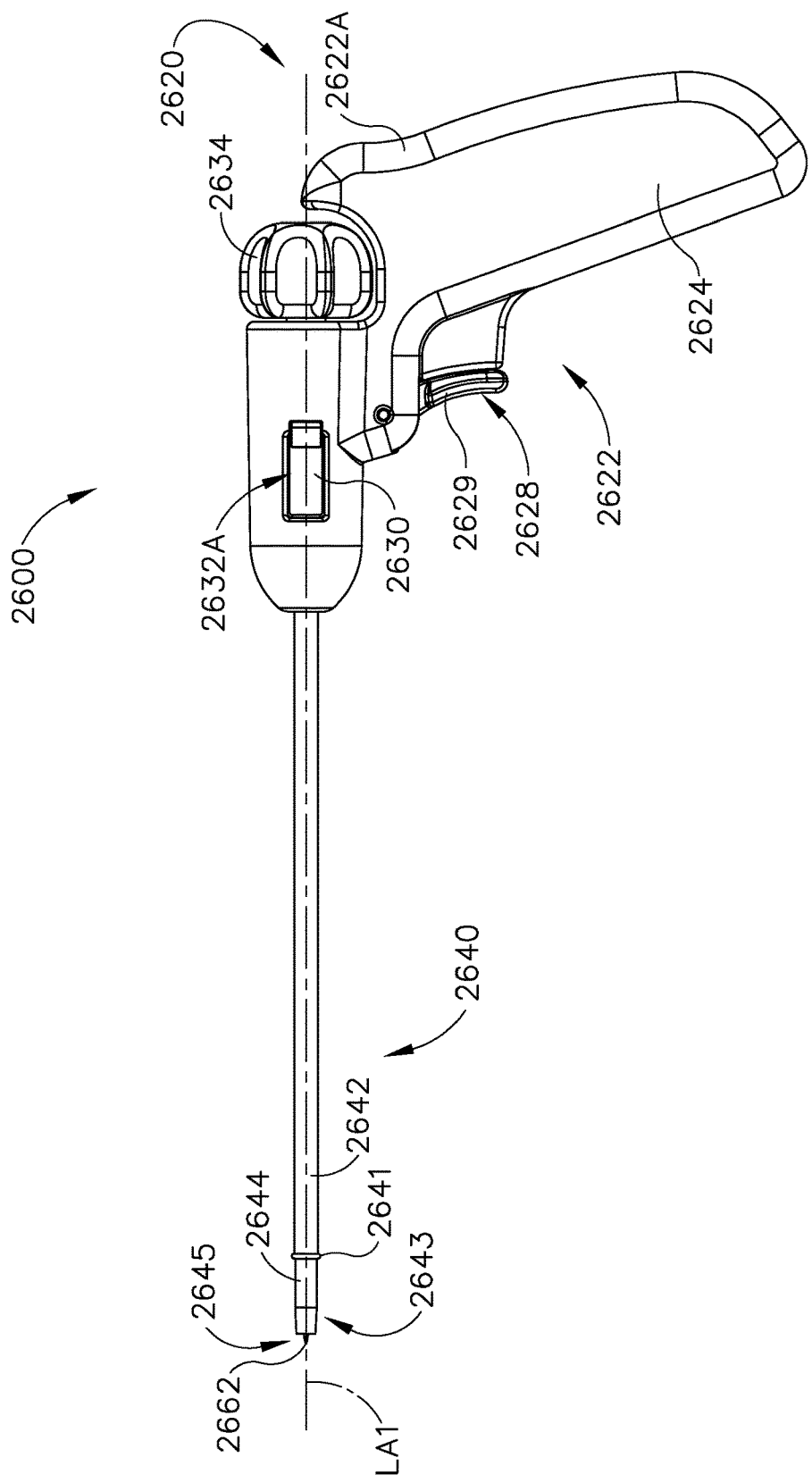
FIG. 4 depicts a side elevational view of the instrument of FIG. 3.
Figure 6:
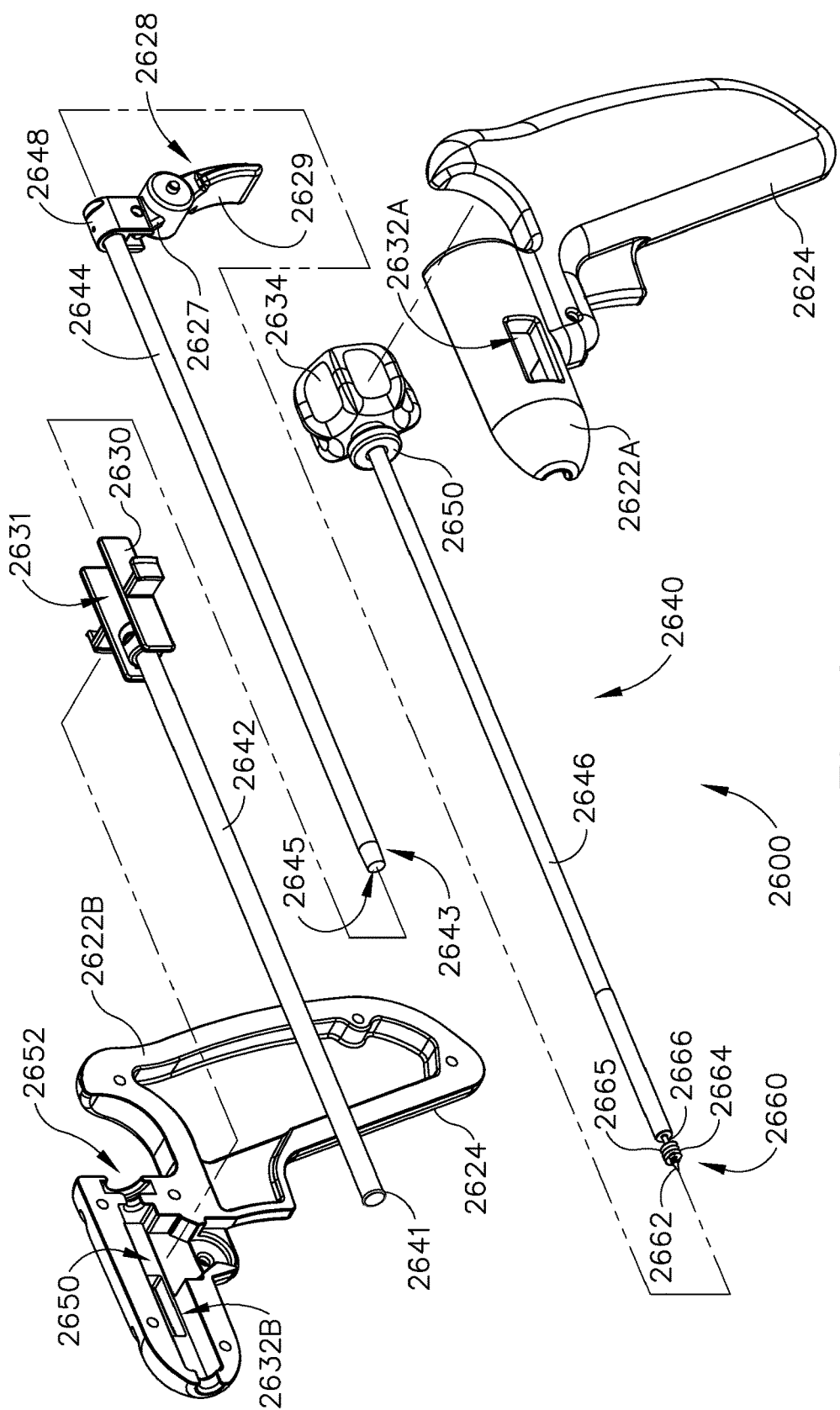
FIG. 6 depicts an exploded perspective view of the instrument of FIG. 3.

FIGS. 3-4 and 6 show an exemplary instrument (2600) that may be used to form an opening in a lamina wall in the sinus cavity such as a sinus wall (SW). The sinus wall (SW) may be a wall of the ethmoid bulla (EB) (e.g., the anterior face of the ethmoid bulla (EB)) or the wall of some other sinus cavity. The instrument (2600) of the present example comprises a handle assembly (2620) and a shaft assembly (2640). The handle assembly (2620) comprises a first body portion (2622A) and a second body portion (2622B) coupled together to form a body (2622). Of course, the handle assembly (2620) may instead be formed of a single body portion or more than two body portions. The body (2622) defines a pistol grip (2624) in the present example, though it should be understood that the body (2622) may alternatively provide a variety of alternative grip configurations.

The handle assembly (2620) further includes a pivoting trigger (2628) that is pivotable toward and away from the pistol grip (2624). As shown in FIGS. 3-6, the pivoting trigger (2628) includes a paddle (2629) extending downwardly from the body (2622) such that a user may actuate the pivoting trigger (2628) with a finger or thumb of a hand that is grasping the pistol grip (2624). As will be discussed in more detail below, actuation of the pivoting trigger (2628) causes longitudinal movement of a cutter tube (2644) of the shaft assembly (2640). The handle assembly (2620) also includes a sliding trigger (2630) that is longitudinally slidable between a proximal position and a distal position within an internal channel (2650) of the body (2622). Portions of the sliding trigger (2630) project laterally from a pair of slots (2632A, 2632B) formed respectively in the first body portion (2622A) and the second body portion (2622B) such that a user may actuate the sliding trigger (2630) with a finger or thumb of a hand that is grasping the pistol grip (2624). As will be discussed in more detail below, actuation of the sliding trigger (2630) causes longitudinal movement of an outer sheath (2642) of shaft assembly (2640). The handle assembly (2620) further includes a rotatable knob (2634) that is rotatable about a longitudinal axis (LA1) defined by the shaft assembly (2640). As will be discussed in more detail below, actuation of the rotatable knob (2634) causes rotation of a rotatable shaft (2646) of the shaft assembly (2640) relative to the handle assembly (2620) and relative to other components of the shaft assembly (2640).

The shaft assembly (2640) extends distally from the handle assembly (2620). As best seen in FIGS. 6-7, the shaft assembly (2640) comprises an outer sheath (2642), a cutter tube (2644), and a rotatable shaft (2646). As best seen in FIG. 6, a proximal end of outer sheath (2642) is unitarily coupled with a distal portion of the sliding trigger (2630) such that longitudinal movement of the sliding trigger (2630) causes concurrent longitudinal sliding of the outer sheath (2642) along the longitudinal axis (LA1). The cutter tube (2644) is slidably disposed within the outer sheath (2642) such that the cutter tube (2644) and the outer sheath (2642) are able to move independently relative to each other along the longitudinal axis (LA1).

Figure 5:
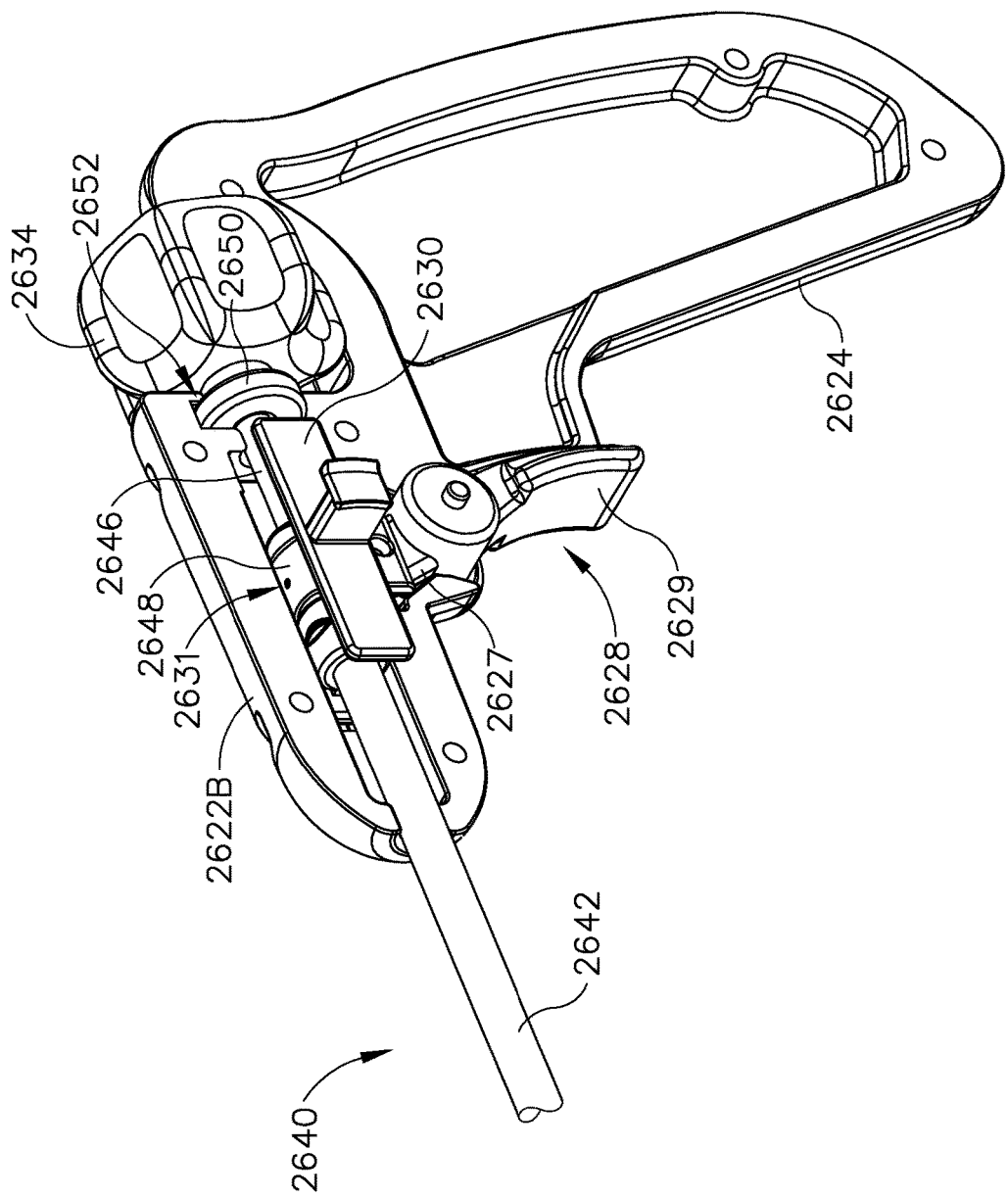
FIG. 5 depicts a detailed perspective view of a handle assembly of the instrument of FIG. 3.

A proximal end of the cutter tube (2644) is integrally coupled with a sliding member (2648). As best seen in FIG. 5, the sliding member (2648) is slidably disposed within a proximal gap (2631) defined by the sliding trigger (2630) such that the sliding member (2648) slides longitudinally within the proximal gap (2631) of the sliding trigger (2630); and such that the sliding member (2648) and the sliding trigger (2630) are able to slide longitudinally independently relative to each other. The sliding member (2648) is pivotably coupled with an arm (2627) extending unitarily from the pivoting trigger (2628) in an opposite direction of the paddle (2629). It should therefore be understood that pivoting the paddle (2629) toward the pistol grip (2624) will cause pivoting of the arm (2627) distally, and vice versa. It should further be understood that, distal pivoting of the arm (2627) will cause distal longitudinal movement of the sliding member (2648) and the cutter tube (2644) along the longitudinal axis (LA1); and proximal pivoting of the arm (2627) will cause proximal longitudinal movement of the sliding member (2648) and the cutter tube (2644) along the longitudinal axis (LA1). In some versions, the pivoting trigger (2628) is biased away from the pistol grip (2624) by a resilient member (not shown) (e.g. a torsion spring, leaf spring, etc.) such that the cutter tube (2644) is biased toward a proximal position. An operator may thus advance the cutter tube (2644) distally relative to the handle assembly (2620) by squeezing the paddle (2629) toward the pistol grip (2624); then retract the cutter tube (2644) proximally by releasing the paddle (2629).

The rotatable shaft (2646) is rotatably disposed within the cutter tube (2644) such that the rotatable shaft (2646) rotates independently relative to the cutter tube (2644) and such that the cutter tube (2644) is capable of moving longitudinally independently relative to the rotatable shaft (2646). A proximal end of the rotatable shaft (2646) is integrally coupled with the rotatable knob (2634) such that rotation of the rotatable knob (2634) causes rotation of the rotatable shaft (2646) about the longitudinal axis (LA1). As best seen in FIG. 6, an annular flange (2652) extends outwardly from a distal portion of the rotatable knob (2634) and is rotatably disposed within an annular pocket (not shown) that is formed in the body (2622), such that the rotatable knob (2634) is capable of rotating yet incapable of moving longitudinally relative to the longitudinal axis (LA1).

The distal end of the outer sheath (2642) includes an outwardly projecting annular bumper (2641). By way of example only, the bumper (2641) may be formed of steel, hard plastic, soft plastic, elastomeric material, etc. Alternatively, the bumper (2641) may be a unitarily formed feature of the outer sheath (2642), with a radiused edge to provide the outer sheath (2642) with an atraumatic distal tip. The bumper (2641) may be used to move anatomical structures (e.g., middle turbinate, uncinate process, etc.) without damaging those anatomical structures as the distal end of the shaft assembly (2640) is advanced to the sinus wall (SW). The bumper (2641) may also soften any forward force that the sheath (2642) might exert on the sinus wall (SW) while the shaft assembly (2640) is being positioned. In some versions, the bumper (2641) and/or the distal end of outer sheath (2642) may be obliquely angled relative to the longitudinal axis of the outer sheath (2642) (e.g., angled from approximately 20° to approximately 70°, etc.), which may facilitate use of bumper (2641) to move tissue. It should also be understood that some versions of the bumper (2641) may extend distally past the distal end of the outer sheath (2642).

A distal portion of the cutter tube (2644) has a tapered distal region (2643) terminating in an opening (2645) that is defined by a sharp annular edge. An auger member (2660) extends distally from a distal end of the rotatable shaft (2646) such that as the rotatable shaft (2646) rotates, the auger member (2660) rotates as well. The auger member (2660) comprises a minor shaft (2666) having a sharp distal tip (2662) and a helical blade or flight (2664) projecting outwardly from the minor shaft (2666). The minor shaft (2666) of the present example has an outer diameter of between approximately 0.04 inches and approximately 0.06 inches, though it should be understood that any other suitable outer diameter may be used. As will be discussed in more detail below, the sharp distal tip (2662) may be used to penetrate the sinus wall (SW). The length of the sharp distal tip (2662) may be configured to avoid inadvertent contact with other portions of the sinus wall (SW). For instance, the sharp distal tip (2662) may have a length of approximately 0.1 inches. Alternatively, any other suitable length may be used.

The helical flight (2664) presents an effective outer diameter (OD) that is substantially similar to an inner diameter defined by the sharp annular distal edge of the cutter tube (2644). By way of example only, the inner diameter defined by the sharp annular distal edge of the cutter tube (2644) may define a gap with the effective outer diameter (OD) of the helical flight (2664) that is between approximately 0.0005 inches and approximately 0.002 inches. In some versions, the inner diameter defined by the sharp annular distal edge of the cutter tube (2644) defines a gap with the effective outer diameter (OD) of the helical flight (2664) that is less than approximately 0.005 inches. The inner diameter of the cutter tube (2644) thus closely complements the effective outer diameter (OD) of the helical flight (2664). Alternatively, any other suitable gap may be provided. In the present example, the gap between the inner diameter defined by the sharp annular distal edge of the cutter tube (2644) and the effective outer diameter (OD) of the helical flight (2664) is dimensioned to prevent any tissue from getting lodged between the inner diameter defined by the sharp annular distal edge of the cutter tube (2644) and the effective outer diameter (OD) of the helical flight (2664). In the present example, the outer diameter (OD) is approximately 0.144 inches, though any other suitable outer diameter (OD) may be used. Also in the present example, the effective outer diameter (OD) is approximately equal to the outer diameter of a major diameter proximal portion (2686). As best seen in FIG. 8, beginning at a distal portion of the helical flight (2664), the helical flight (2664) gradually projects further from the outwardly minor shaft (2666) until reaching the outer diameter (OD). In some versions, the distal-most portion of the helical flight (2664) begins in a region where the tip (2662) slopes inwardly from the outer diameter of minor shaft (2666) (i.e., such that the distal end of helical flight (2664) terminates within the conical tapered region of the tip (2662)). It should be understood that the depicted version of the helical flight (2664) is merely illustrative; and that the helical flight (2664) may have any suitable flight pitch.

The auger member (2660) of the present example also defines a longitudinal gap extending longitudinally between a proximal end of the helical flight (2664) and the distal end of the rotatable shaft (2646). The gap between the proximal end of the helical flight (2664) and the distal end of the rotatable shaft (2646) of the present example has a length of approximately 0.040 inches, though it should be understood that the gap may have any other suitable length. An exterior edge of the helical flight (2664) in the present example presents a flat surface (2665). Flat surface (2665) of the present example has a width between approximately 0.002 inches and approximately 0.005 inches. Alternatively, any other suitable width may be used. As will be discussed in more detail below, the helical flight (2664) is configured to guide and drive the auger member (2660) through an opening formed in the sinus wall (SW) by the sharp distal tip (2662); and to provide a structural anchor for the instrument (2600) within the sinus wall (SW).

Figure 9A:
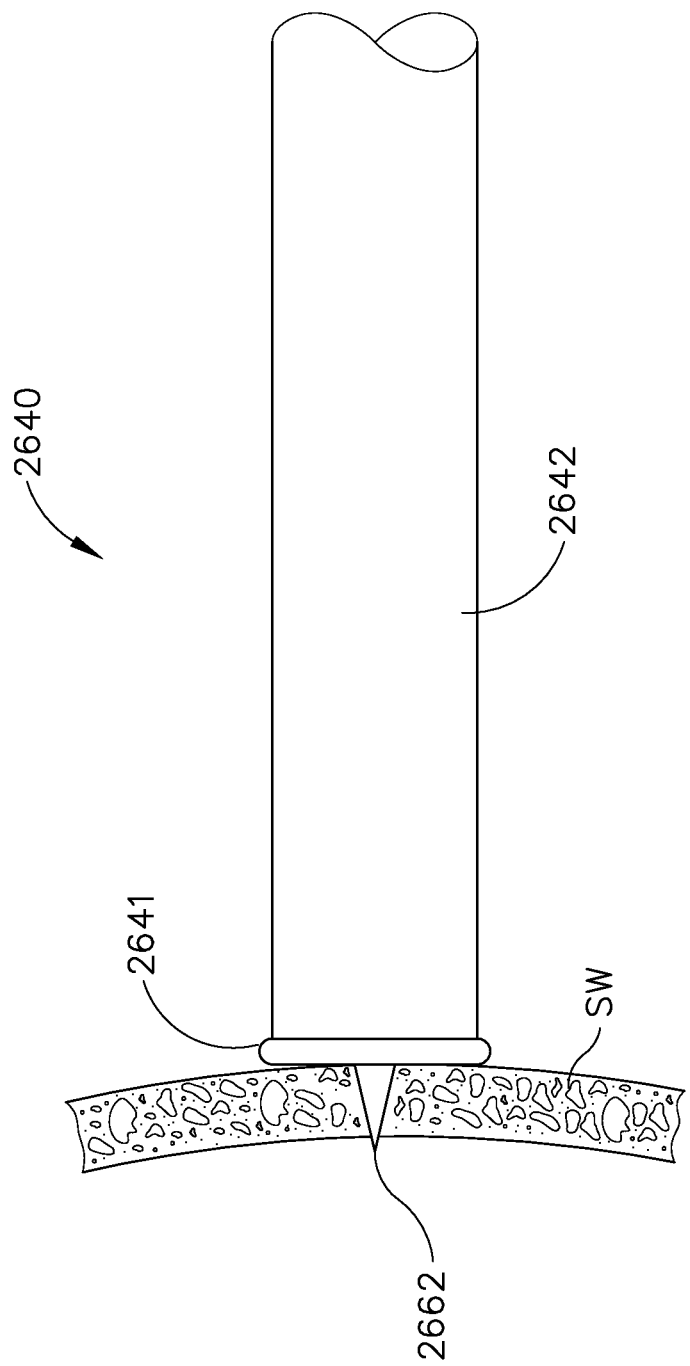
FIG. 9A depicts a side elevational view of the shaft assembly of FIG. 7 in a first longitudinal position, with an outer sheath and a cutter of the shaft assembly also in a first longitudinal position.
Figure 9B:
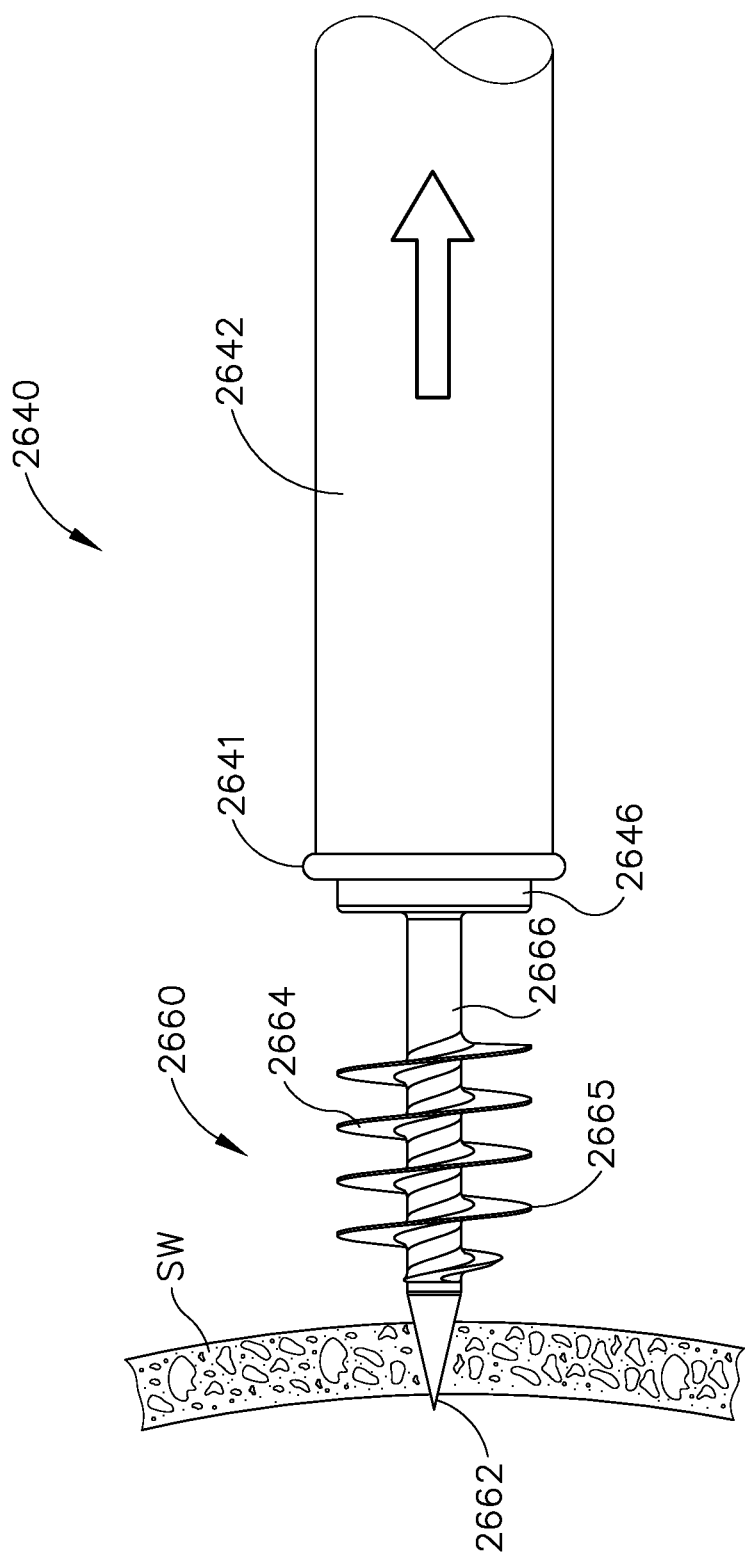
FIG. 9B depicts a side elevational view of the shaft assembly of FIG. 7 in the first longitudinal position, with the outer sheath moved to a second longitudinal position, and with the cutter still in the first longitudinal position.
Figure 9C:
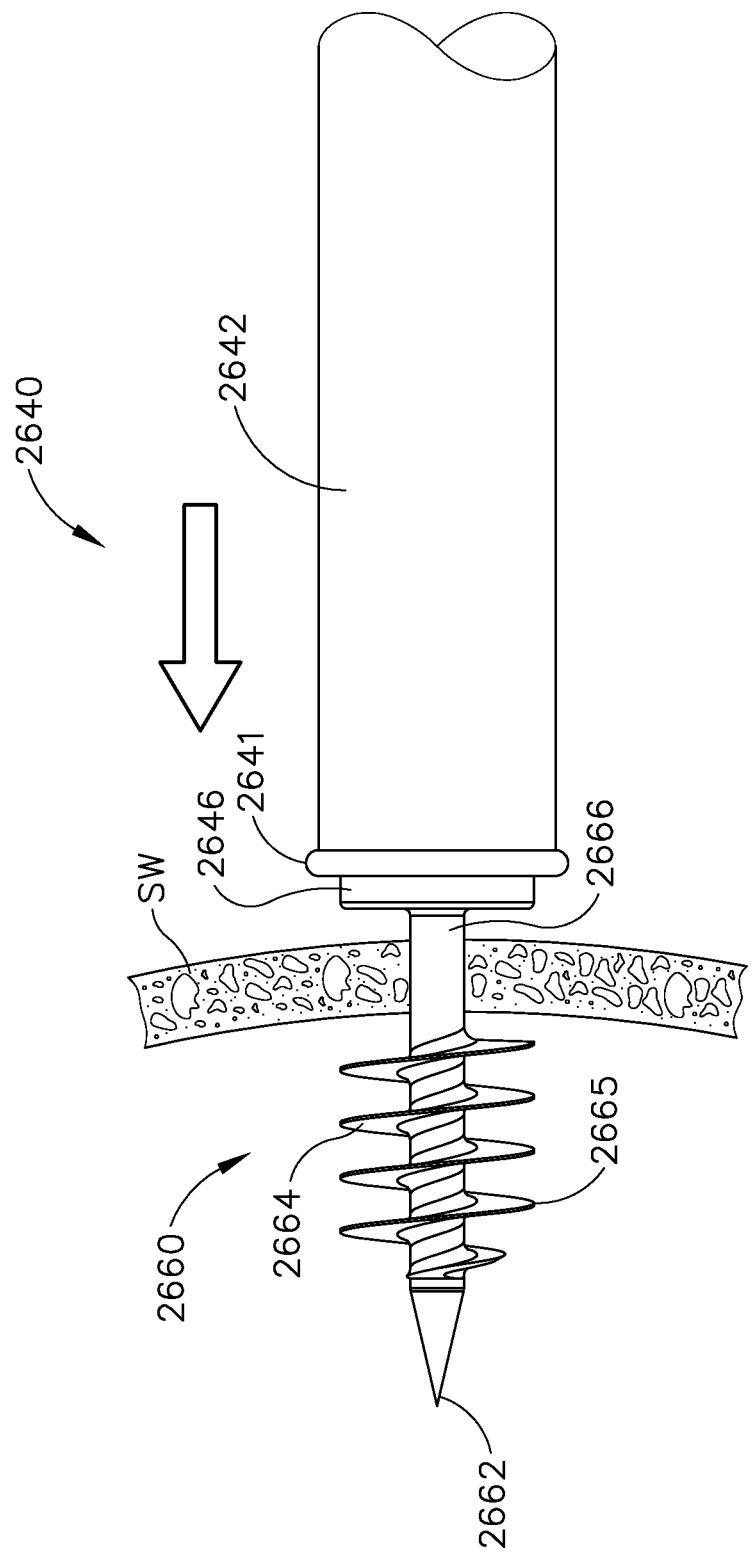
FIG. 9C depicts a side elevational view of the shaft assembly of FIG. 7 moved to a second longitudinal position, with the outer sheath still in the second longitudinal position, and with the cutter still in the first longitudinal position.
Figure 10A:
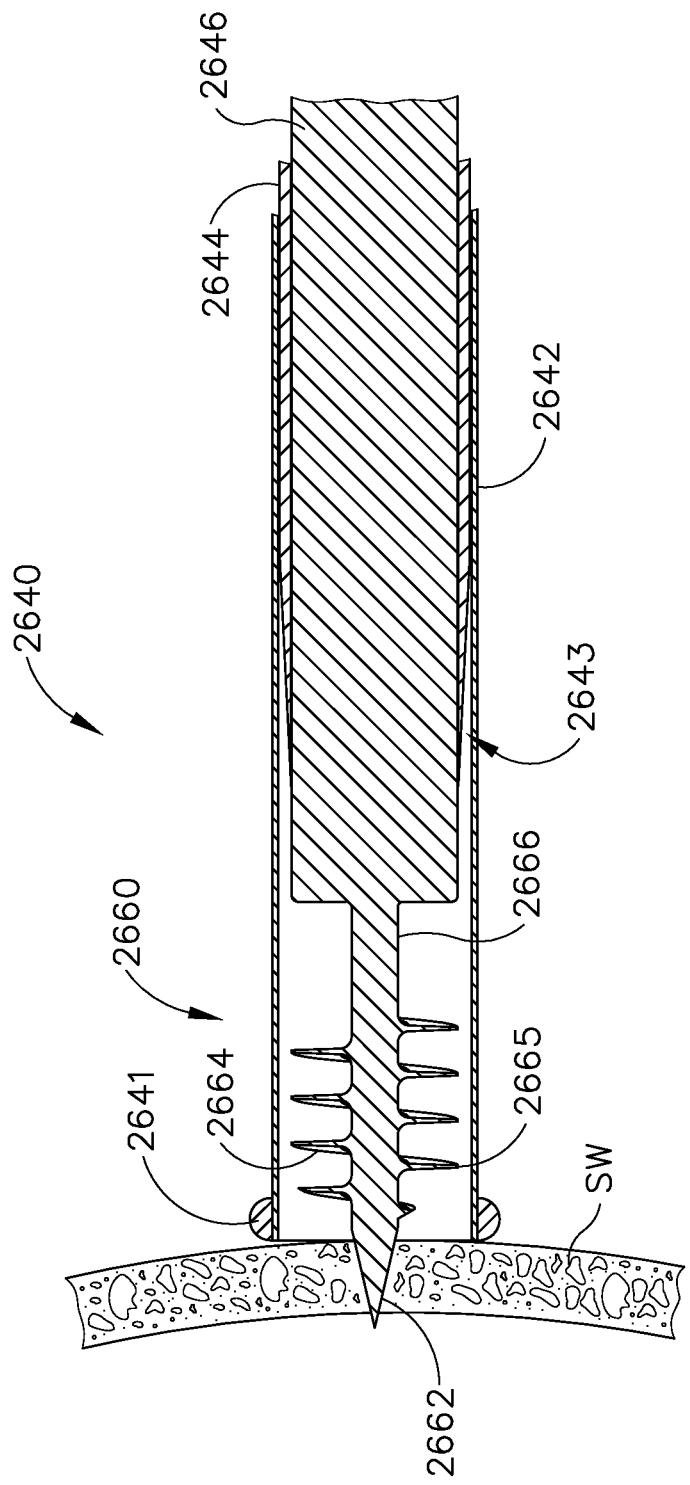
FIG. 10A depicts a side cross-sectional view of the shaft assembly of FIG. 7 in a first longitudinal position, with an outer sheath and a cutter of the shaft assembly also in a first longitudinal position.
Figure 10B:
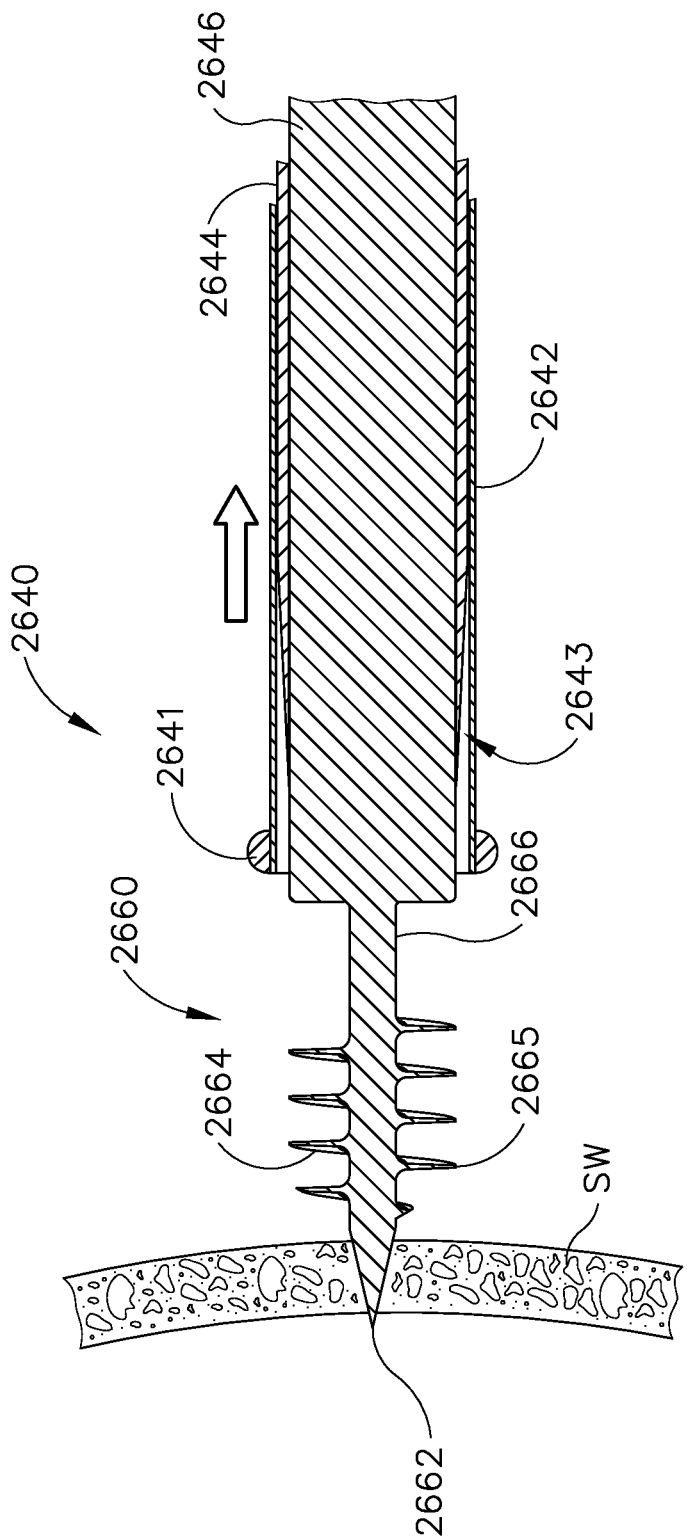
FIG. 10B depicts a side cross-sectional view of the shaft assembly of FIG. 7 in the first longitudinal position, with the outer sheath moved to a second longitudinal position, and with the cutter still in the first longitudinal position.
Figure 10C:
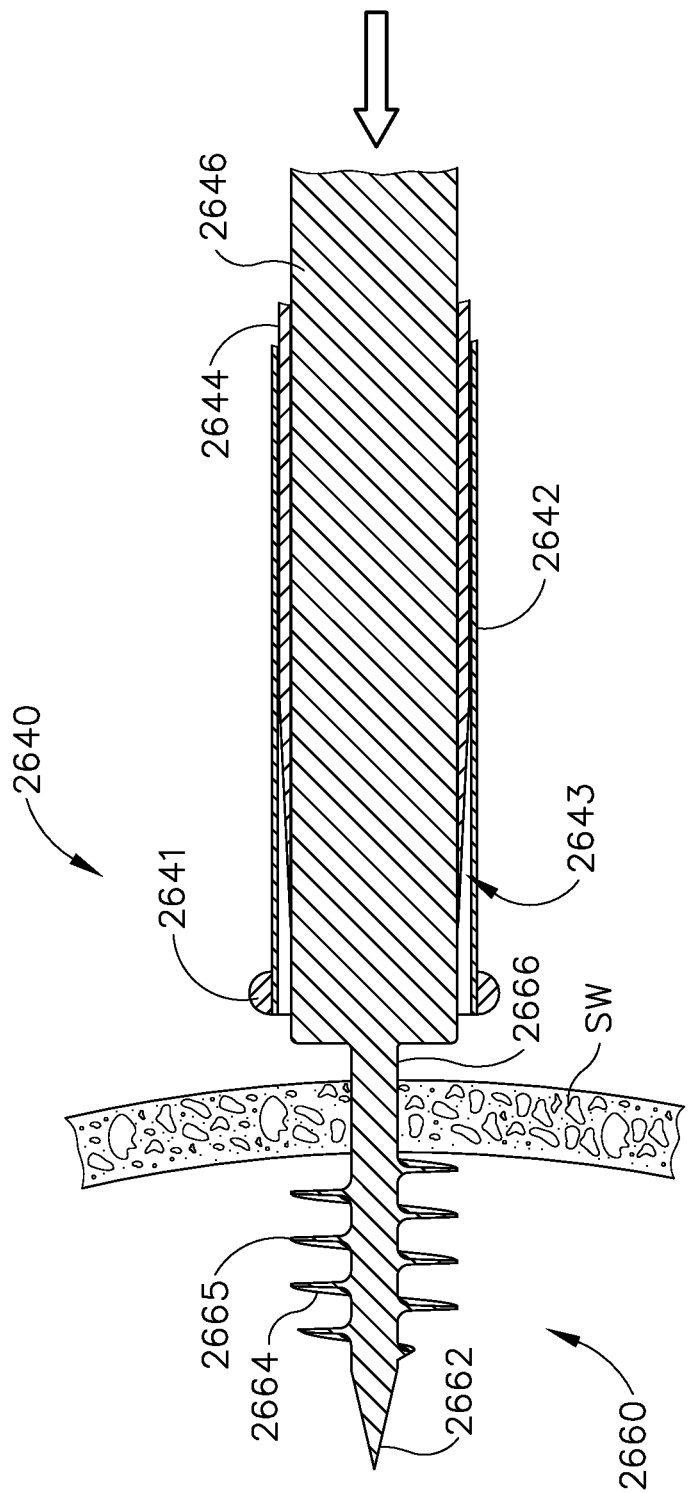
FIG. 10C depicts a side cross-sectional view of the shaft assembly of FIG. 7 moved to a second longitudinal position, with the outer sheath still in the second longitudinal position, and with the cutter still in the first longitudinal position.

1. Exemplary Operation of Instrument with Helical Auger and Retractable Sheath As shown in FIGS. 9A and 10A, the instrument (2600) may be initially positioned such that the circular bumper (2641) of the outer sheath (2642) is at the sinus wall (SW) with the outer sheath (2642) partially covering the auger member (2660) such that only a distal portion of the sharp distal tip (2662) penetrates the sinus wall (SW). In some versions, the outer sheath (2642) is configured to completely cover the sharp distal tip (2662) until the distal end of the shaft assembly (2640) reaches the sinus wall (SW). Once the sharp distal tip (2662) initially pierces the sinus wall (SW), the outer sheath (2642) is fully retracted proximally by moving the sliding trigger (2630) longitudinally proximally, thus completely exposing the auger member (2660) as shown in FIGS. 9B and 10B. The auger member (2660) is then rotated and advanced distally by rotating the rotatable knob (2634) and advancing the instrument (2600) distally. It should be understood that, after initially piercing the sinus wall (SW) with the sharp distal tip (2662), the auger member (2660) continues to advance distally by rotating due to the helical configuration of the flight (2664). In particular, the helical flight (2664) is driven through the sinus wall (SW) like a screw until the sinus wall (SW) is positioned within the longitudinal gap between the proximal end of the helical flight (2664) and the distal end of the rotatable shaft (2646), as shown in FIGS. 9C and 10C. In some other exemplary uses, distal advancement of the instrument (2600) ceases before the sinus wall (SW) reaches the longitudinal gap between the proximal end of the helical flight (2664) and the distal end of the rotatable shaft (2646). It should be understood that the auger member (2660) may be advanced through the sinus wall (SW) solely due to rotation of the auger member (2660), such that the operator need not also press distally on any portion of the instrument (2600) as the flight (2664) traverses the sinus wall (SW).

Figure 10D:
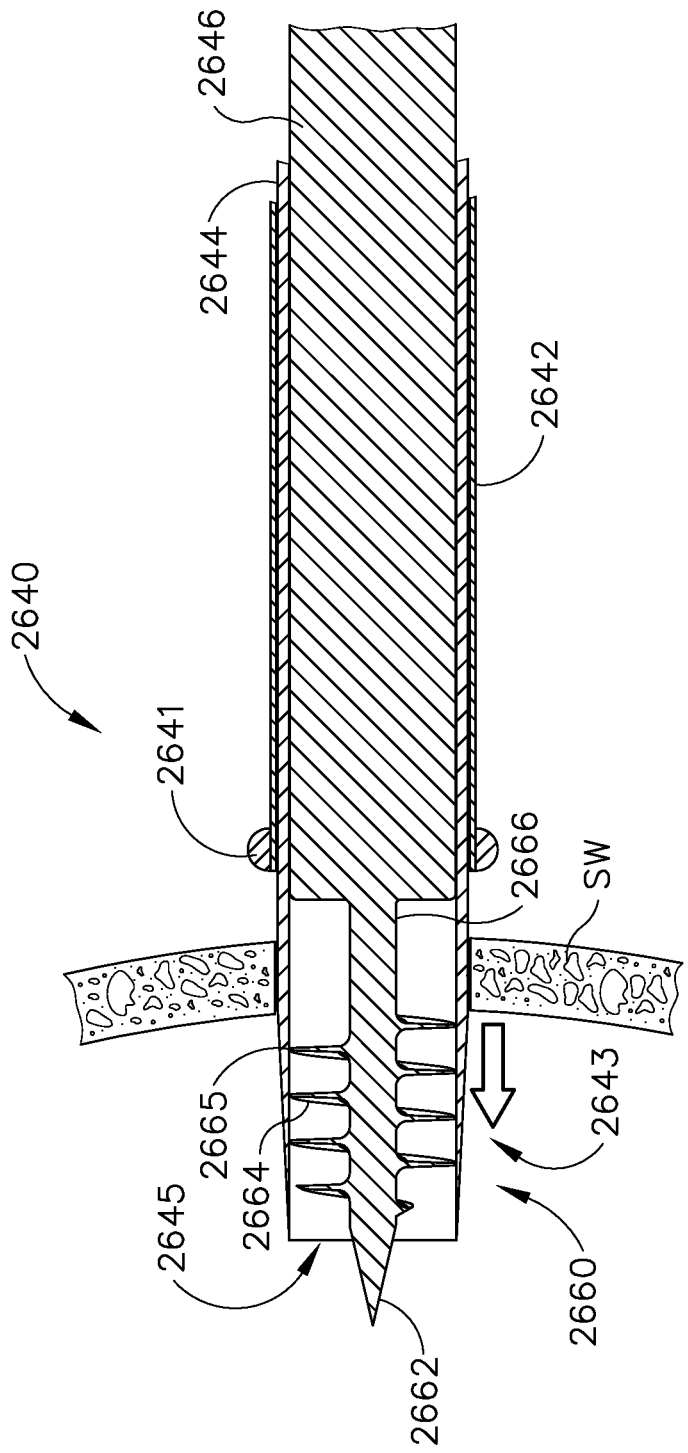
FIG. 10D depicts a side cross-sectional view of the shaft assembly of FIG. 7 in the second longitudinal position, with the outer sheath still in the second longitudinal position, and with the cutter moved to a second longitudinal position.
Figure 11:
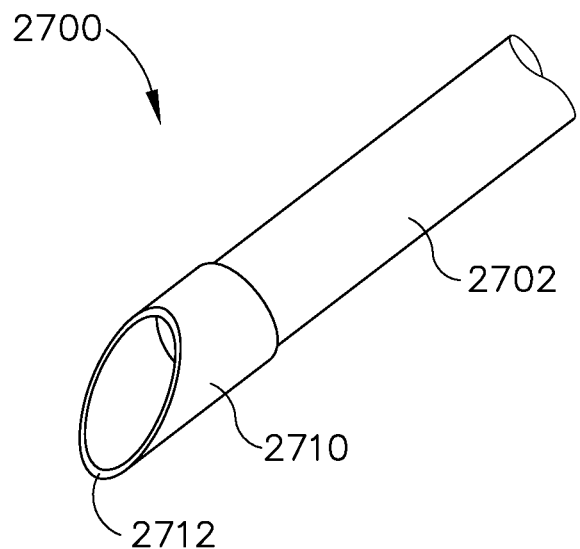
FIG. 11 depicts a perspective view of an exemplary alternative outer sheath assembly that may be used with the instrument of FIG. 3.
Figure 12:
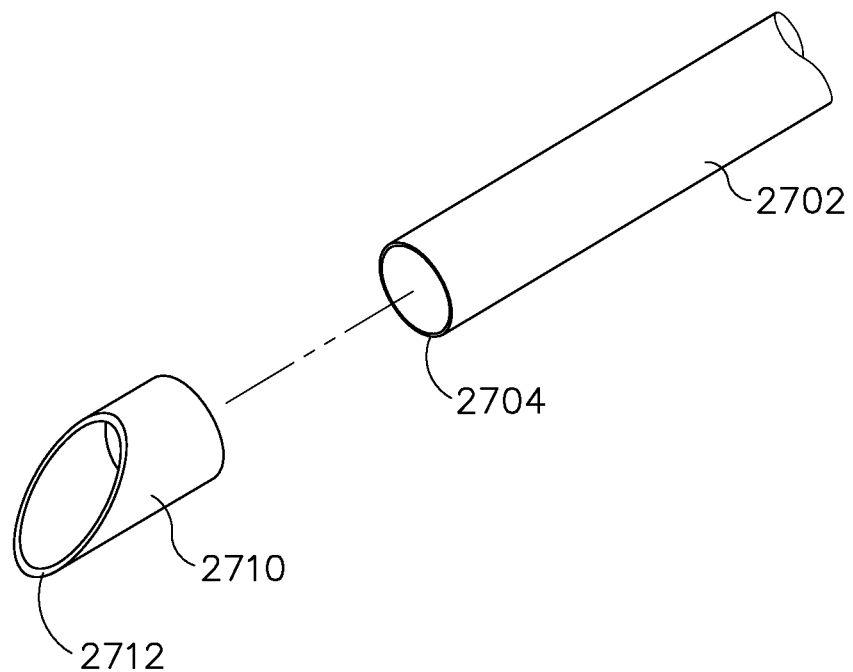
FIG. 12 depicts an exploded view of the outer sheath assembly of FIG. 11.

To the stage shown in FIGS. 9C and 10C, the cutter tube (2644) has remained stationary relative to the outer sheath (2642). The outer sheath (2642) has thus protected tissue from inadvertent contact with the sharp distal end of the cutter tube (2644). However, once the auger member (2660) has been driven through sinus wall (SW), the cutter tube (2644) is then advanced distally relative to the outer sheath (2642) and the rotatable shaft (2646) by squeezing the pivoting trigger (2628) toward the pistol grip (2624) while the auger member (2660) remains stationary. In some versions, the cutter tube (2644) rotates while it advances distally; while in other versions it does not. In versions of the cutter tube (2644) that rotate, the cutter tube (2644) may comprise cutting features—e.g. serrations—along the sharp edge defining the opening (2645). When the cutter tube (2644) advances distally, the sharp edge defining the opening (2645) passes through the sinus wall (SW) until the tapered region (2643) has fully traversed the sinus wall (SW), as shown in FIGS. 9D and 10D. During this advancement of the cutter tube (2644), the auger member (2660) anchors the instrument (2600) in the sinus wall (SW) and may further provide structural support to the sinus wall (SW) as the cutter tube (2644) traverses the sinus wall (SW). The tapered region (2643) provides a gradual widening of the opening in the sinus wall (SW). The instrument (2600) is then withdrawn from the sinus wall (SW), leaving behind an opening (2670). In some instances, the tapered configuration of the distal region (2643) drives some adjacent soft tissue away from the bone of the sinus wall (SW) as the cutter tube (2644) is advanced distally through the sinus wall (SW), such that the soft tissue returns to position and covers the edge of the bone at the opening (2670) when the shaft assembly (2640) is withdrawn from the opening (2670).

It should be understood that the auger member (2660) and/or the cutter tube (2644) may be driven to any depth desired. For instance, the auger member (2660) and the cutter tube (2644) may be driven through two or more sinus walls (SW) (e.g., along the same longitudinal path) in succession (e.g., forming a first opening in the first sinus wall (SW), then advancing distally to subsequently form a second opening in a second sinus wall (SW) after the first opening is complete, etc.). It should also be understood that, once the opening (2670) has been initially formed, the operator may retract the cutter tube (2644), position an edge of the opening (2670) in a gap defined along the length of the minor shaft (2666) between the proximal end of flight (2664) and the distal end of the major diameter portion of rotatable shaft (2646), then advance the cutter tube (2644) distally to thereby take a bite out of the edge of the opening (2670). This will enlarge the size of opening (2670) and may be repeated as desired in order to provide a selected size and configuration for the opening (2670). Various other suitable features of the instrument (2600) and methods of using the instrument (2600) will be apparent to those of ordinary skill in the art in view of the teachings herein.

Although the outer sheath (2642) of the present example is driven by the sliding trigger (2360), it should be understood that the outer sheath (2642) may be driven by other methods. For instance, the outer sheath (2642) may be driven proximally, thus exposing the cutter tube (2646), via rotation of the rotatable knob (2634). The outer sheath (2642) may also comprise a tapered distal portion that covers the auger member (2660) to thereby further facilitate insertion of the shaft assembly (2640) into tight places. While the sheath (2642) of the present example is rigid (e.g., formed of rigid plastic or stainless steel, etc.), the outer sheath (2642) may alternatively be flexible to thereby further facilitate insertion of the shaft assembly (2640) into tight places. Such a flexible outer sheath (2642) may comprise a slidable "exoskeleton" to selectively prevent flexibility when rigidity is necessary. Such a flexible outer sheath may further comprise internal features that cause the outer sheath (2642) to flex outwardly as the cutter tube (2646) is driven distally to avoid cutting of the outer sheath (2642). It should also be understood that the sheath (2642) may include detent features or similar features that provide some degree of resistance to sliding the sheath (2642) when the sheath (2642) is in a proximal position and/or when the sheath (2642) is in a distal position. Other suitable variations will be apparent to those of ordinary skill in the art in view of the teachings herein.

2. Exemplary Alternative Retractable Sheath

FIGS. 11-14E depict an exemplary alternative sheath assembly (2700) that may be readily incorporated into the shaft assembly (2640) of the instrument (2600), in place of the outer sheath (2642). The sheath assembly (2700) of this example comprises a tube (2702) and a tip member (2710) positioned at the distal end (2704) of tube (2702). The tip member (2710) includes a distal edge (2712) that defines a plane that is oriented at an oblique angle relative to the longitudinal axis of tube (2702). By way of example only, the plane of the distal edge (2712) may be oriented at anywhere between approximately 45 degrees and approximately 60 degrees relative to the longitudinal axis of tube (2702). In some instances, the oblique orientation of the distal edge (2712) may facilitate navigation of the shaft assembly (2640) through the paranasal cavity. For instance, the distal edge (2712) may act as a cam, thereby driving anatomical structures out of the way as a lead-in for further insertion of the tube (2702).

The tip member (2710) may be formed of a variety of materials, including but not limited to pebax, plastic, metal, etc., including combinations thereof. Various suitable materials that may be used to form the tip member (2710) will be apparent to those of ordinary skill in the art in view of the teachings herein. It should also be understood that the tip member (2710) may be secured to the tube (2702) in a variety of ways, including but not limited to overmolding, interference fitting, snap fitting, adhesives, welding, etc. Various suitable ways in which the tip member (2710) may be secured to the tube (2702) will be apparent to those of ordinary skill in the art in view of the teachings herein. In some other variations, the distal edge (2407) of the tube (2702) is formed at an oblique angle. In some such versions, the tip member (2710) is omitted.

Figure 13A:
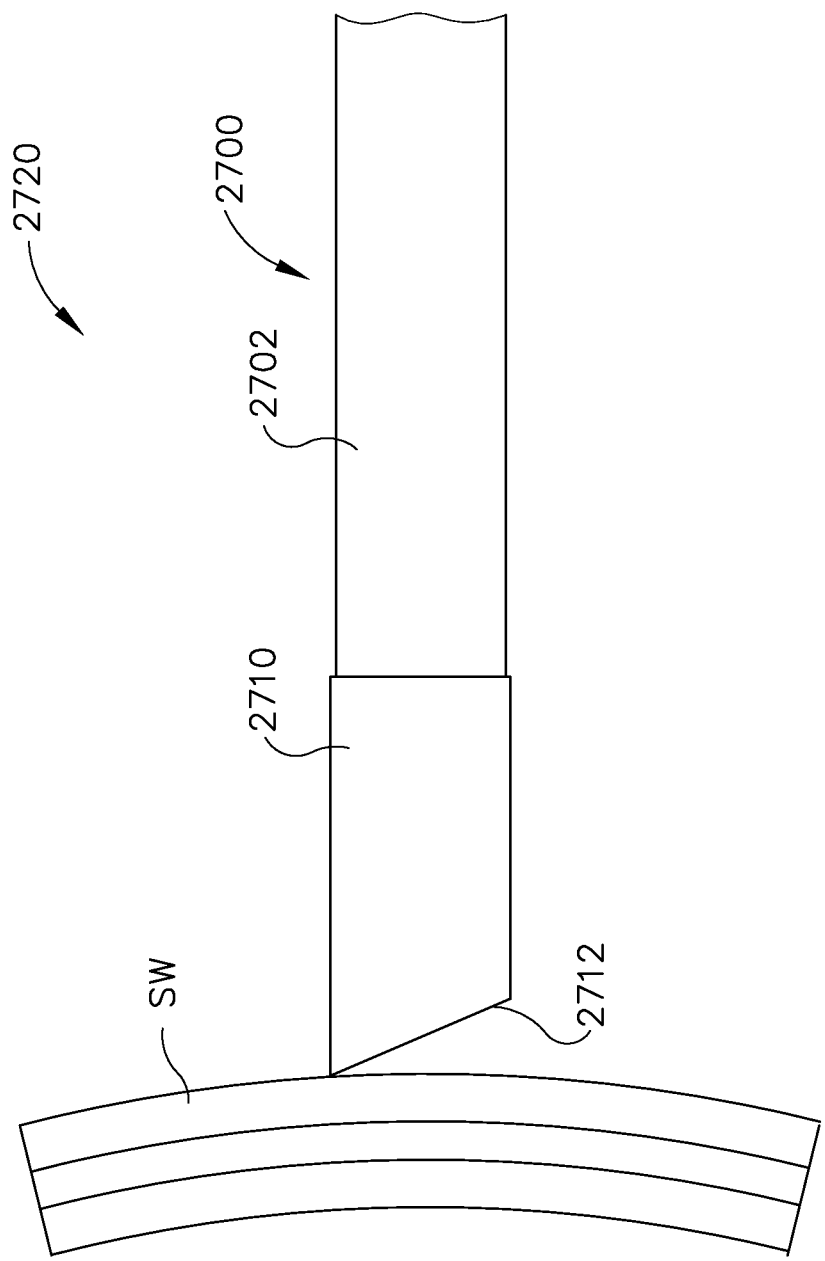
FIG. 13A depicts a side elevational view of the shaft assembly of FIG. 7, incorporating the outer sheath assembly of FIG. 11, with the entire shaft assembly in a first longitudinal position.
Figure 13B:
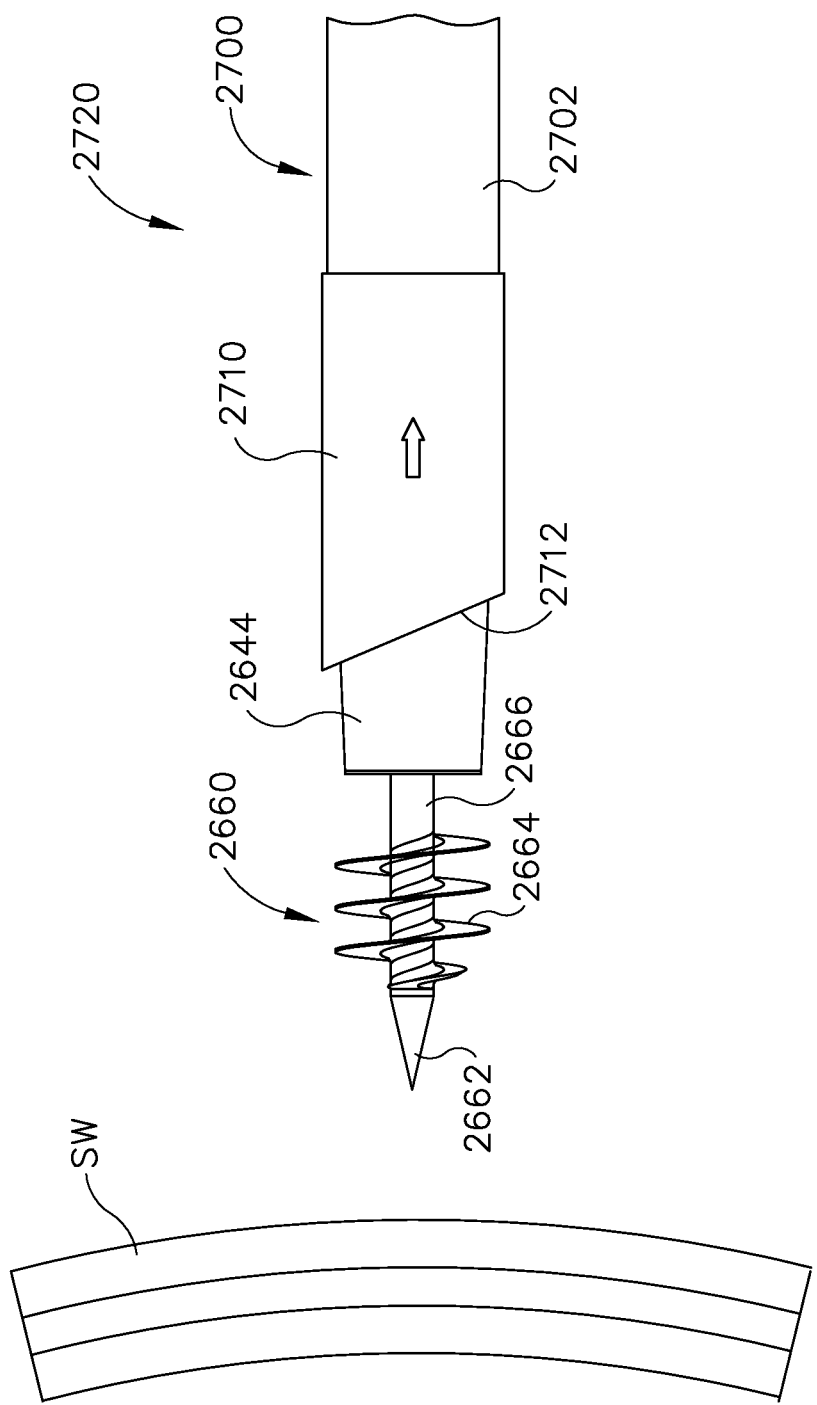
FIG. 13B depicts a side elevational view of the shaft assembly of FIG. 7, incorporating the outer sheath assembly of FIG. 11, with the outer sheath assembly retracted proximally while the rest of the shaft assembly remains in the first longitudinal position.

FIGS. 13A-14E show a shaft assembly (2720) that incorporates the sheath assembly (2700), being used to form an opening in a sinus wall (SW). The sinus wall (SW) may be a wall of the ethmoid bulla (EB) (e.g., the anterior face of the ethmoid bulla (EB)) or the wall of some other sinus cavity. In this example, the shaft assembly (2720) is identical to the shaft assembly (2640), except that the shaft assembly (2720) of this example includes the sheath assembly (2700) instead of the sheath (2642). As shown in FIGS. 13A and 14A, the shaft assembly (2720) is initially positioned such that the distal-most portion of the distal edge (2712) contacts the sinus wall (SW). Up to this point, the auger member (2660) and the cutter tube (2644) are covered by the sheath assembly (2700). Then, the sheath assembly (2700) is retracted proximally (e.g., by moving the sliding trigger (2630) longitudinally proximally), thereby revealing the auger member (2660) and the distal end of the cutter tube (2644) as shown in FIGS. 13B and 14B.

Figure 13C:
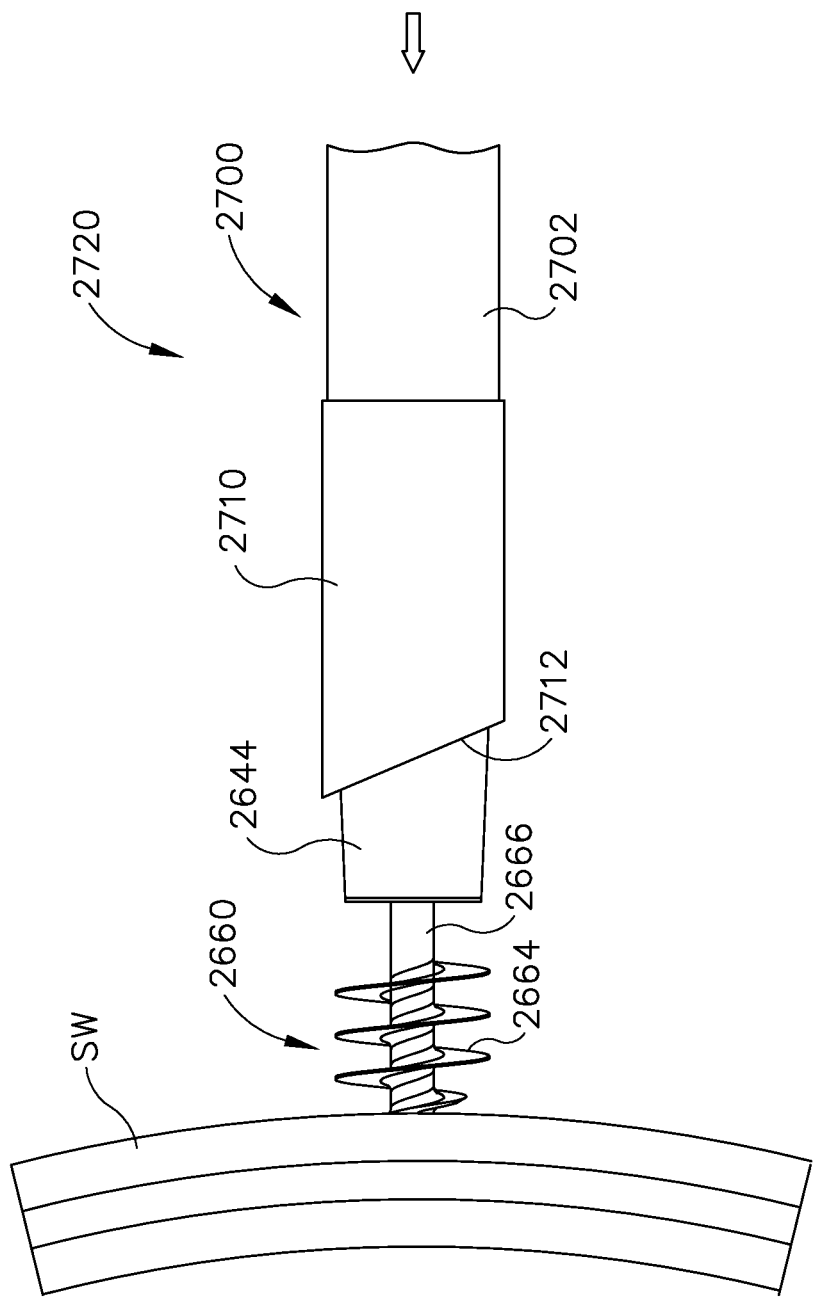
FIG. 13C depicts a side elevational view of the shaft assembly of FIG. 7, incorporating the outer sheath assembly of FIG. 11, with the entire shaft assembly advanced to a second longitudinal position.
Figure 13D:
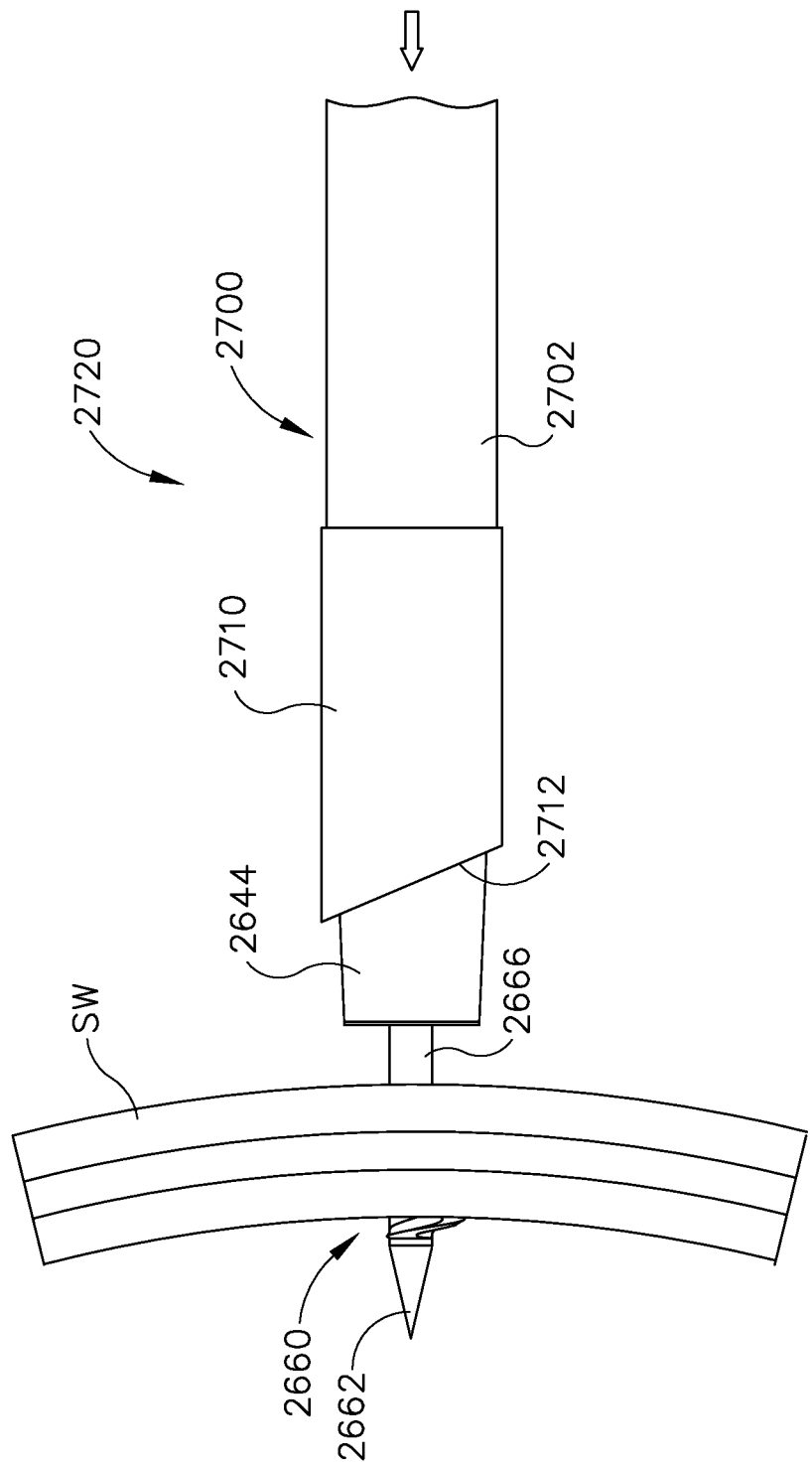
FIG. 13D depicts a side elevational view of the shaft assembly of FIG. 7, incorporating the outer sheath assembly of FIG. 11, with the entire shaft assembly advanced to a third longitudinal position.
Figure 14A:
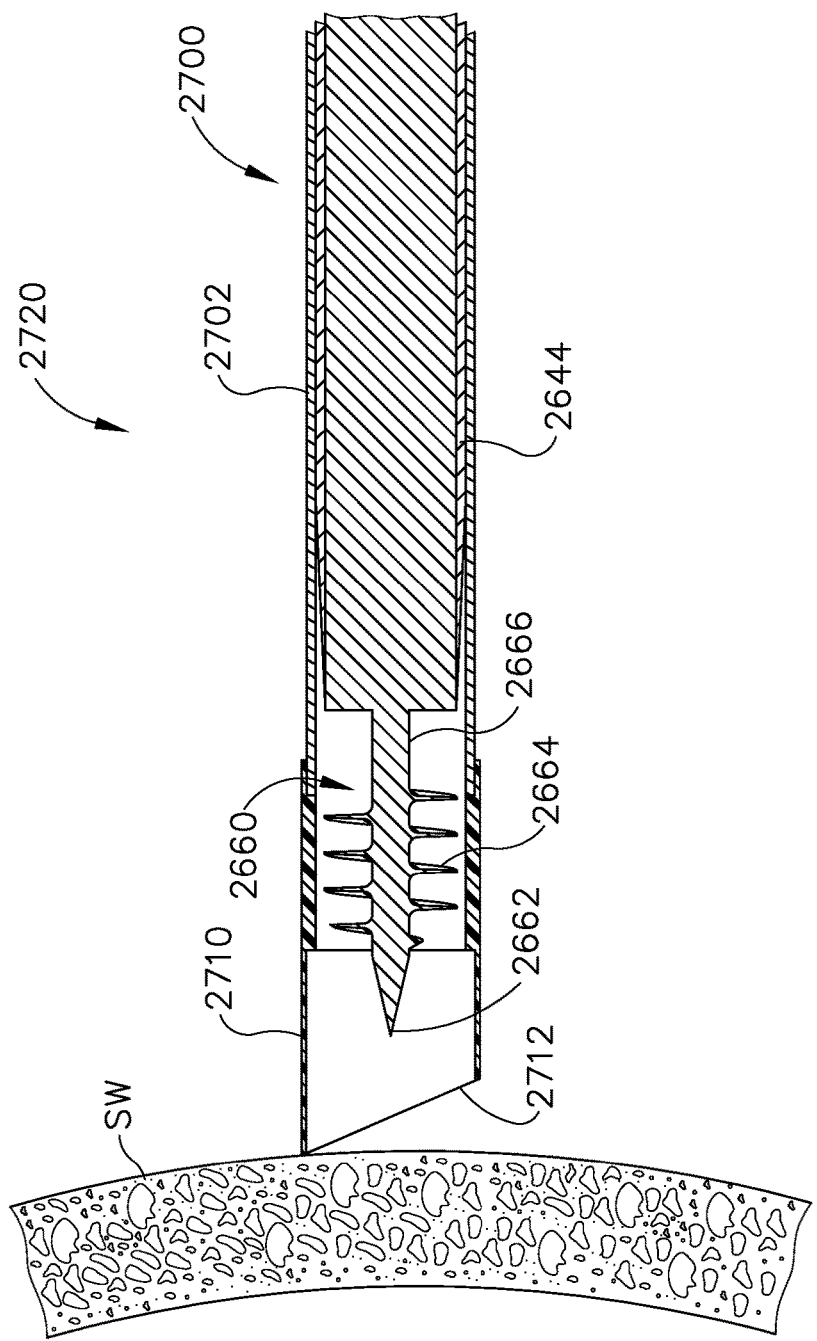
FIG. 14A depicts a side cross-sectional view of the shaft assembly of FIG. 7, incorporating the outer sheath assembly of FIG. 11, with the entire shaft assembly in the first longitudinal position.
Figure 14B:
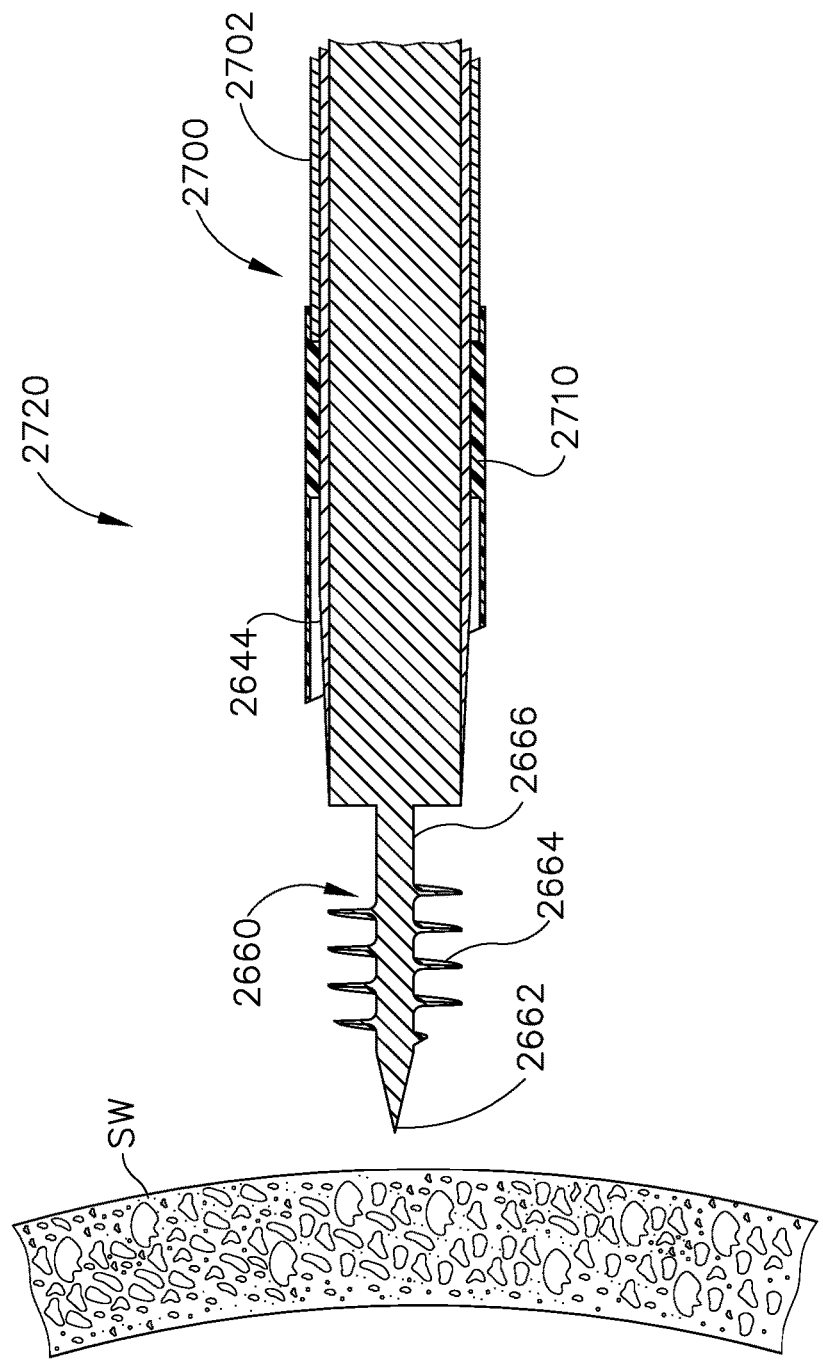
FIG. 14B depicts a side cross-sectional view of the shaft assembly of FIG. 7, incorporating the outer sheath assembly of FIG. 11, with the outer sheath assembly retracted proximally while the rest of the shaft assembly remains in the first longitudinal position.
Figure 14C:
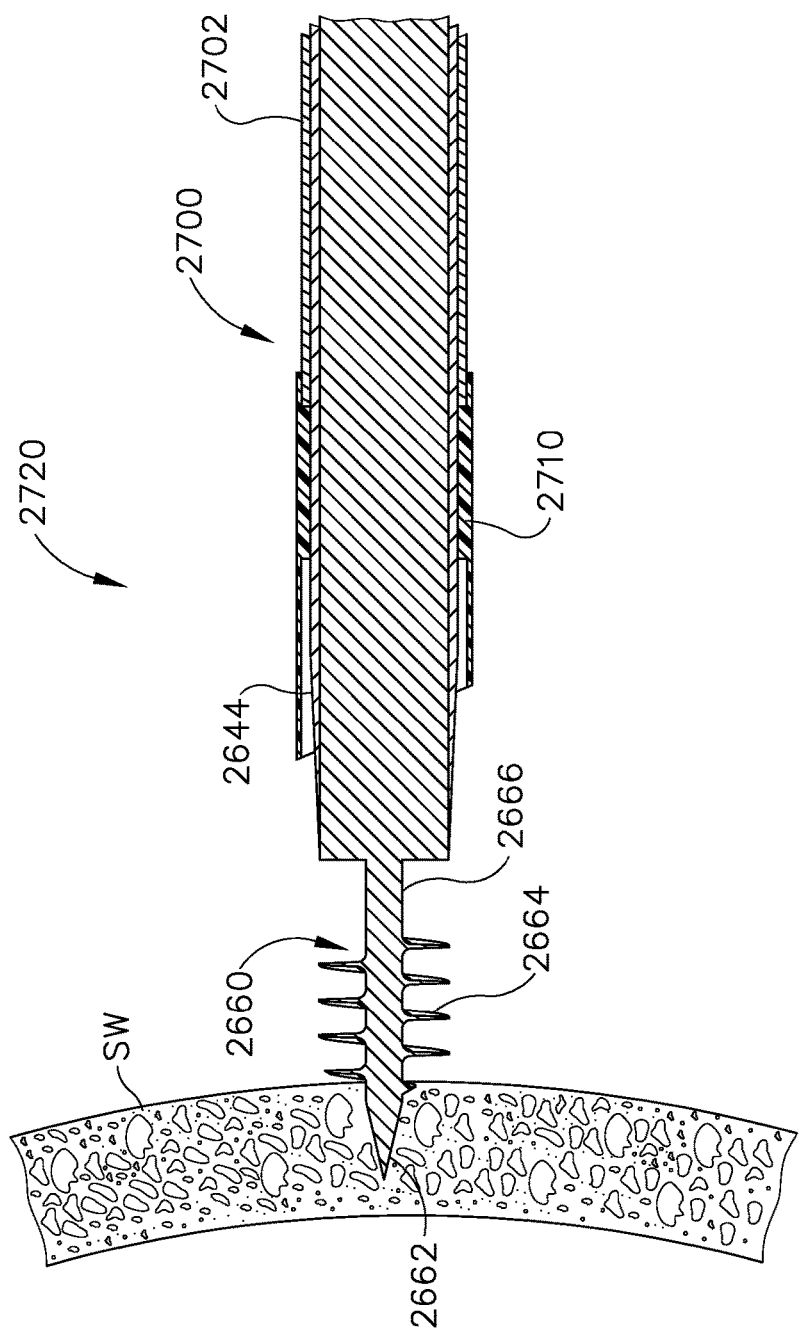
FIG. 14C depicts a side cross-sectional view of the shaft assembly of FIG. 7, incorporating the outer sheath assembly of FIG. 11, with the entire shaft assembly advanced to the second longitudinal position.

With the sheath assembly (2700) retracted, the entire shaft assembly (2720) is advanced distally toward the sinus wall (SW), until the sharp distal tip (2662) of the auger member (2660) pierces the sinus wall (SW) as shown in FIGS. 13C and 14C. With the tip (2662) in the sinus wall (SW), the operator continues to advance the entire shaft assembly (2720) while rotating the auger member (2660) about the longitudinal axis of the shaft assembly (2720) (e.g., by rotating the rotatable knob (2634)). It should be understood that, after initially piercing the sinus wall (SW) with the sharp distal tip (2662), the auger member (2660) continues to advance distally by rotating due to the helical configuration of the flight (2664). In particular, the helical flight (2664) is driven through the sinus wall (SW) like a screw. The auger member (2660) eventually reaches the position shown in FIGS. 13D and 14D, where the flight (2644) is located within the sinus wall (SW). In some instances, the operator stops rotating the auger member (2660) and stops advancing the entire shaft assembly (2720) at this stage. In other words, the region of the minor shaft (2666) proximal to the flight (2664) does not reach the sinus wall (SW) in some instances. In some other instances, the operator rotates the auger member (2660) and continues to advance the entire shaft assembly (2720) until the sinus wall (SW) is positioned about the region of the minor shaft (2666) proximal to the flight (2664). In either case, it should be understood that the auger member (2660) may be advanced through the sinus wall (SW) solely due to rotation of the auger member (2660), such that the operator need not also press distally on any portion of the instrument (2600) as the flight (2664) traverses the sinus wall (SW).

Figure 13E:
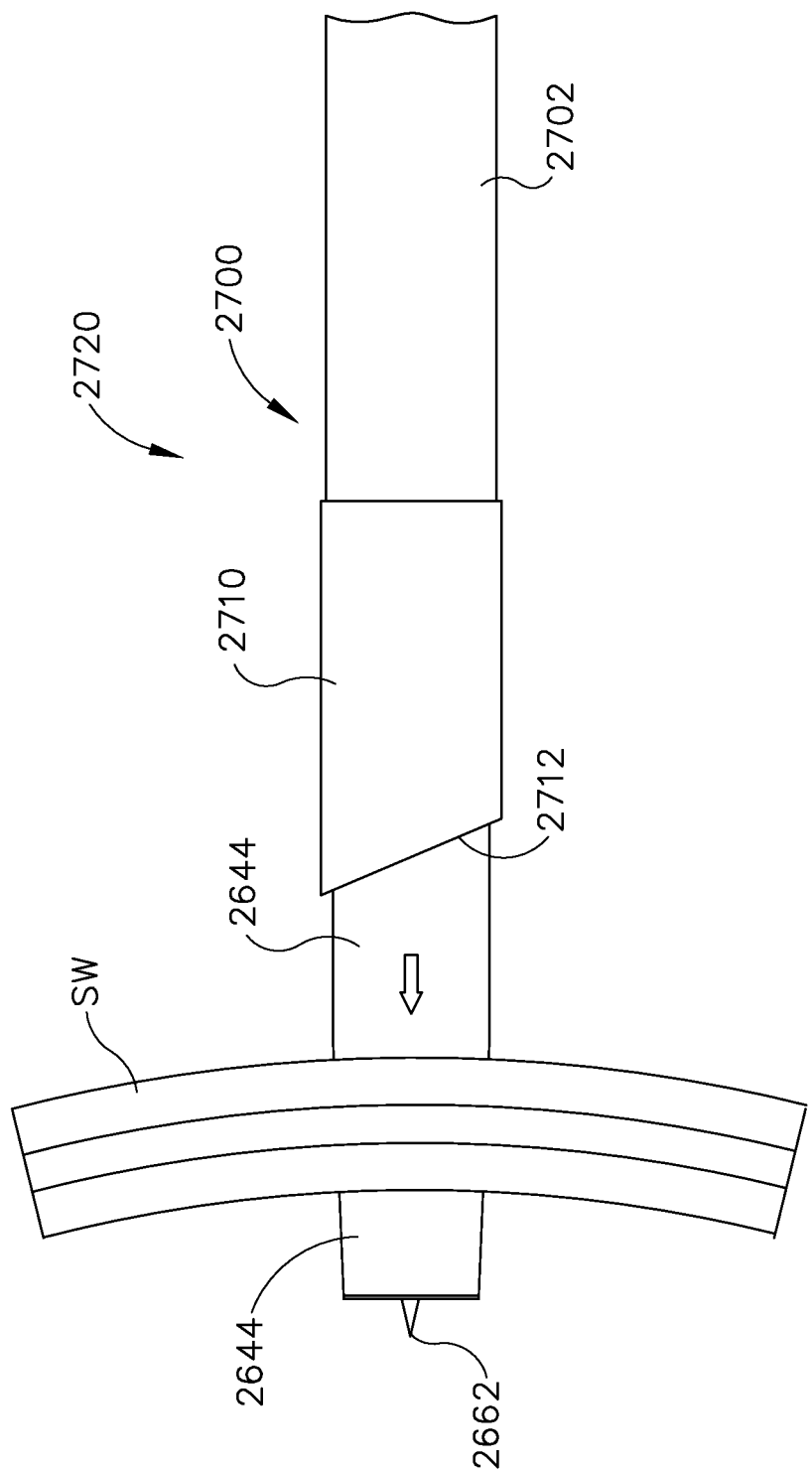
FIG. 13E depicts a side elevational view of the shaft assembly of FIG. 7, incorporating the outer sheath assembly of FIG. 11, with the cutter advanced distally while the rest of the shaft assembly remains in the third longitudinal position.
Figure 14D:
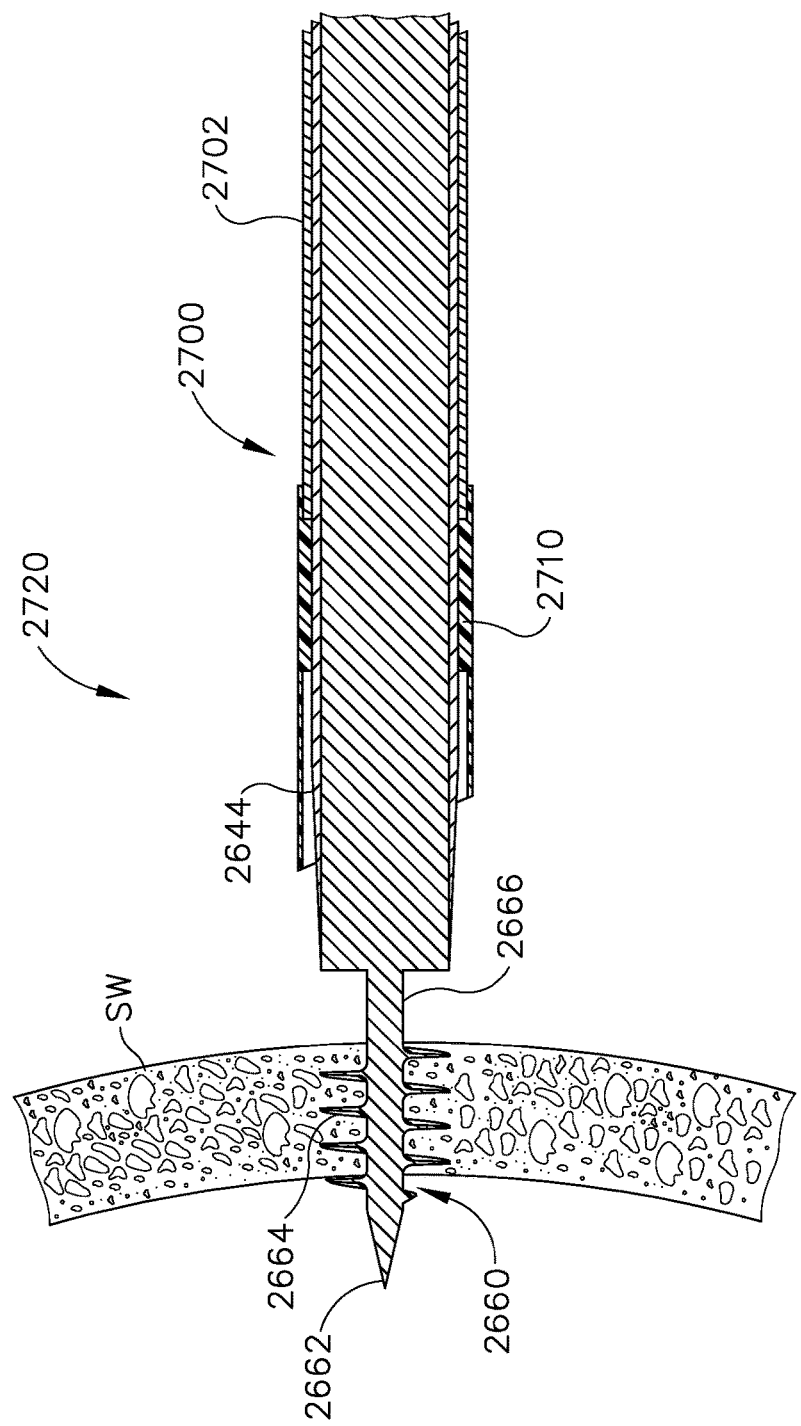
FIG. 14D depicts a side cross-sectional view of the shaft assembly of FIG. 7, incorporating the outer sheath assembly of FIG. 11, with the entire shaft assembly advanced to the third longitudinal position.
Figure 14E:
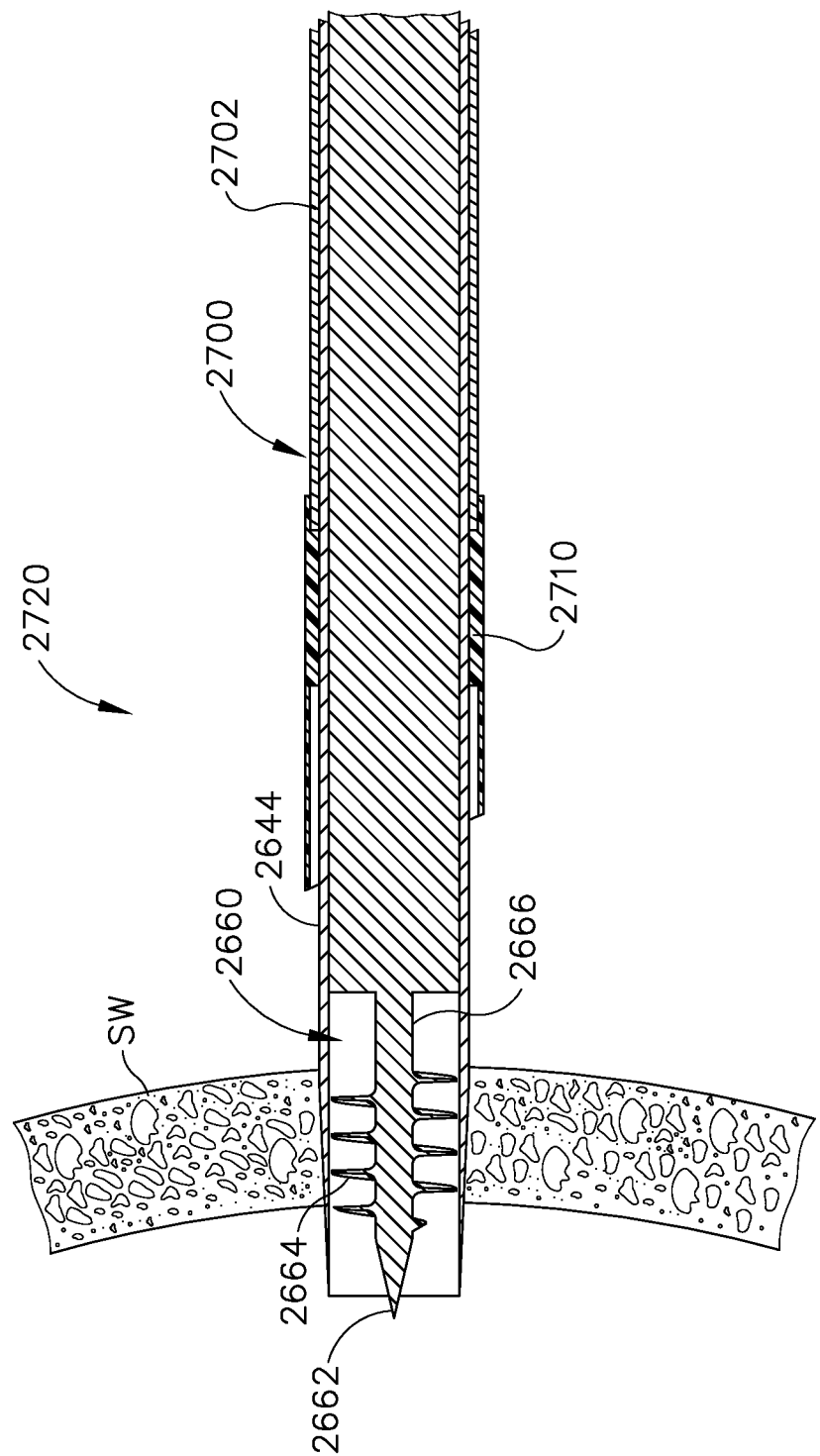
FIG. 14E depicts a side cross-sectional view of the shaft assembly of FIG. 7, incorporating the outer sheath assembly of FIG. 11, with the cutter advanced distally while the rest of the shaft assembly remains in the third longitudinal position.
Figure 14F:
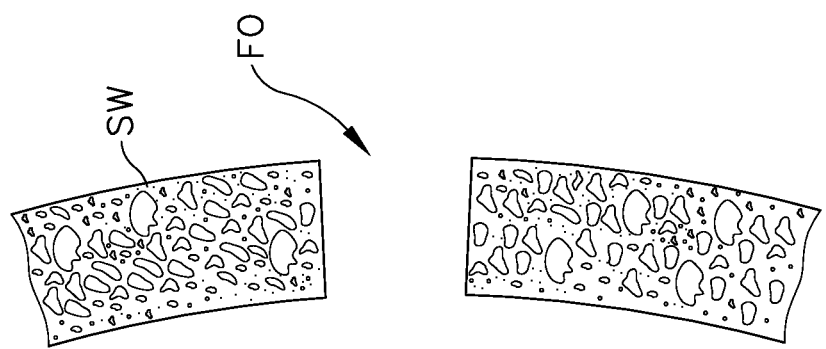
FIG. 14F depicts a side cross-sectional view of a sinus wall with an opening formed by the shaft assembly of FIG. 7.

Having reached the stage shown in FIGS. 13D and 14D, the operator advances the cutter tube (2644) distally (e.g., by squeezing of pivoting trigger (2628) toward the pistol grip (2624)) while holding the remainder of shaft assembly (2720) stationary. The cutter tube (2644) thereby cuts a circular opening in the sinus wall (SW), slicing through the bone and tissue of the sinus wall (SW), as shown in FIGS. 13E and 14E. During this advancement of the cutter tube (2644), the auger member (2660) anchors the shaft assembly (2720) in the sinus wall (SW) and may further provide structural support to the sinus wall (SW) as the cutter tube (2644) traverses the sinus wall (SW). After the cutter tube (2644) cuts through the sinus wall (SW), the entire shaft assembly (2720) is retracted proximally to reveal the formed opening (FO) in the sinus wall (SW), as shown in FIG. 14F. The shaft assembly (2720) may then be cleaned, disposed of, or otherwise handled.

II. OVERVIEW OF EXEMPLARY INSTRUMENT WITH HELICAL AUGER HAVING FLUID PASSAGES

Figure 15:
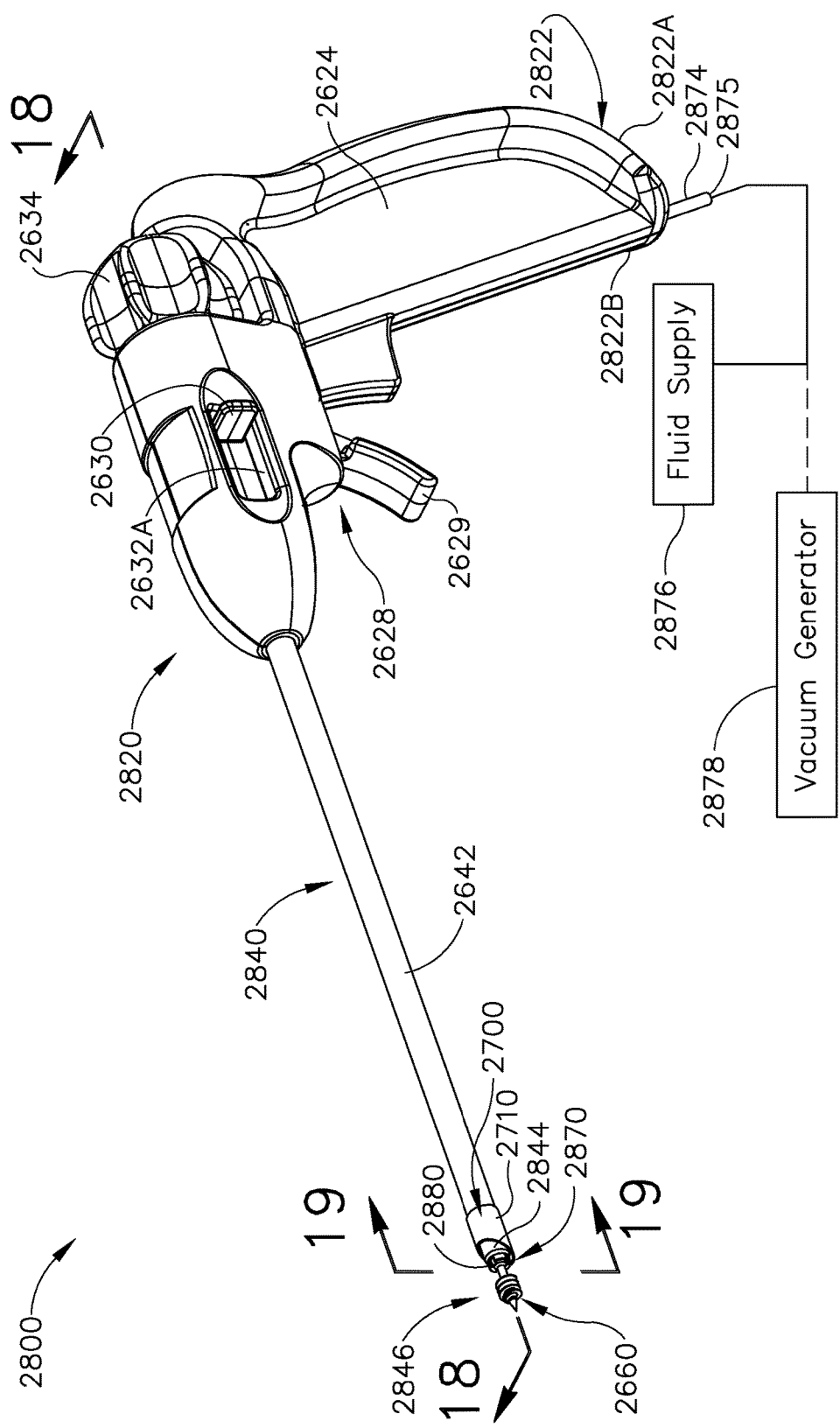
FIG. 15 depicts a perspective view of another exemplary sinus wall piercing instrument.

In some instances, it may be desirable to provide irrigation and/or suction through an opening (FO) that is formed in the ethmoid bulla (EB) and/or through some other opening formed in the nasal cavity using an instrument like instrument (2600). To that end, FIG. 15 shows another exemplary instrument (2800), which is a variation of instrument (2600) that is capable of providing irrigation and/or suction. Instrument (2800) of this example comprises a handle assembly (2820) and a shaft assembly (2840) and is operable to treat a sinus cavity of a patient, such as by opening, irrigating, and suctioning the ethmoid bulla (EB). By way of example, the instrument (2800) may incorporate many of the features discussed above with respect to the instrument (2600) for cutting the opening (FO) into the sinus wall (SW), with the addition of a fluid passage (2870) for irrigating and suctioning the sinus cavity. The instrument (2800) thereby provides for immediate irrigation and suction of the sinus cavity following formation of the opening (FO), without having to remove the instrument that formed the opening (FO) and insert another instrument to provide irrigation or suction. It should be understood that the various features described above may be readily incorporated into the instrument (2800), discussed below in greater detail. As such, the following like numbers indicate like features described above.

Figure 16:
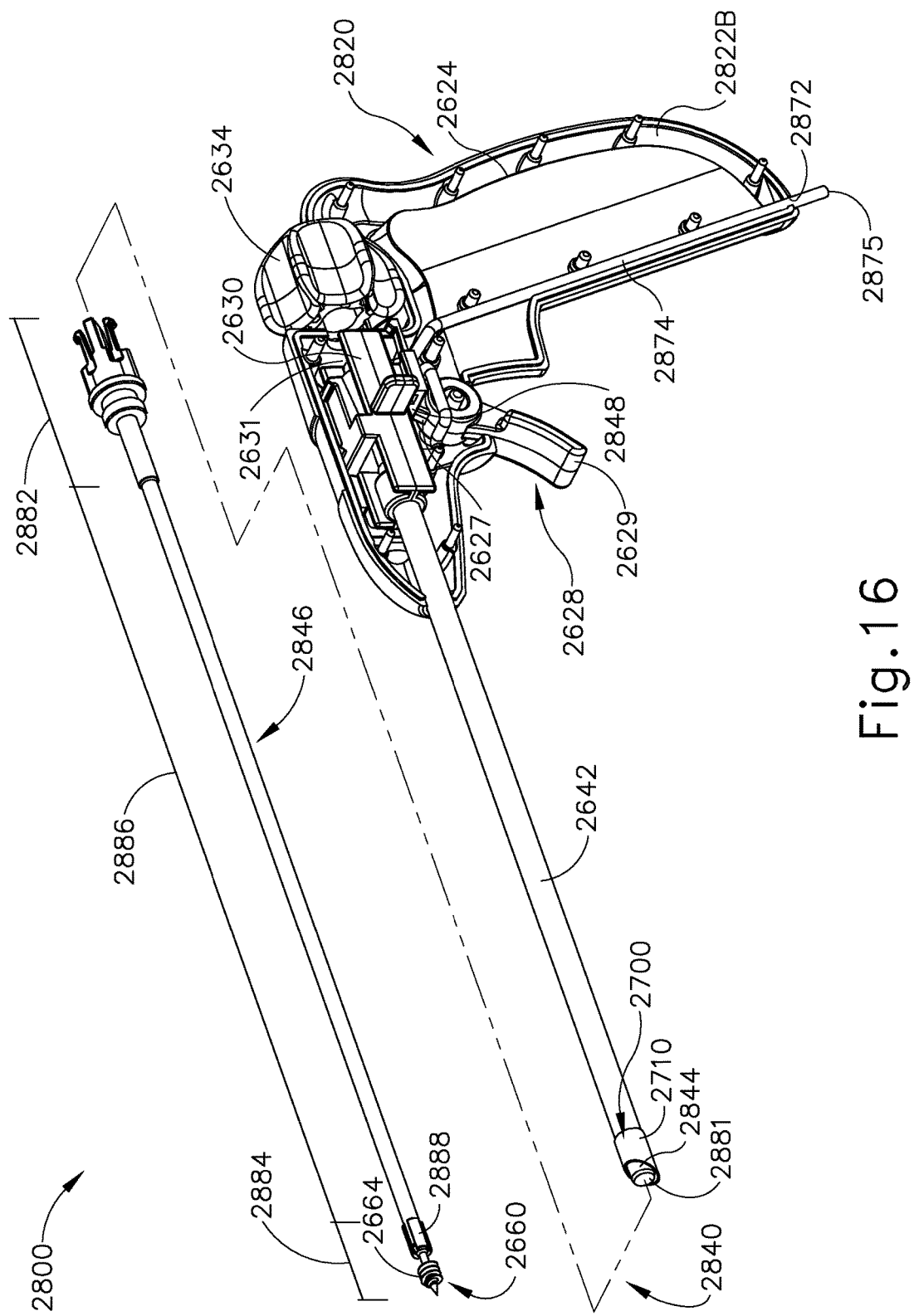
FIG. 16 depicts a partially exploded perspective view of the shaft assembly of the instrument of FIG. 15, with a portion of the handle assembly omitted.
Figure 17:
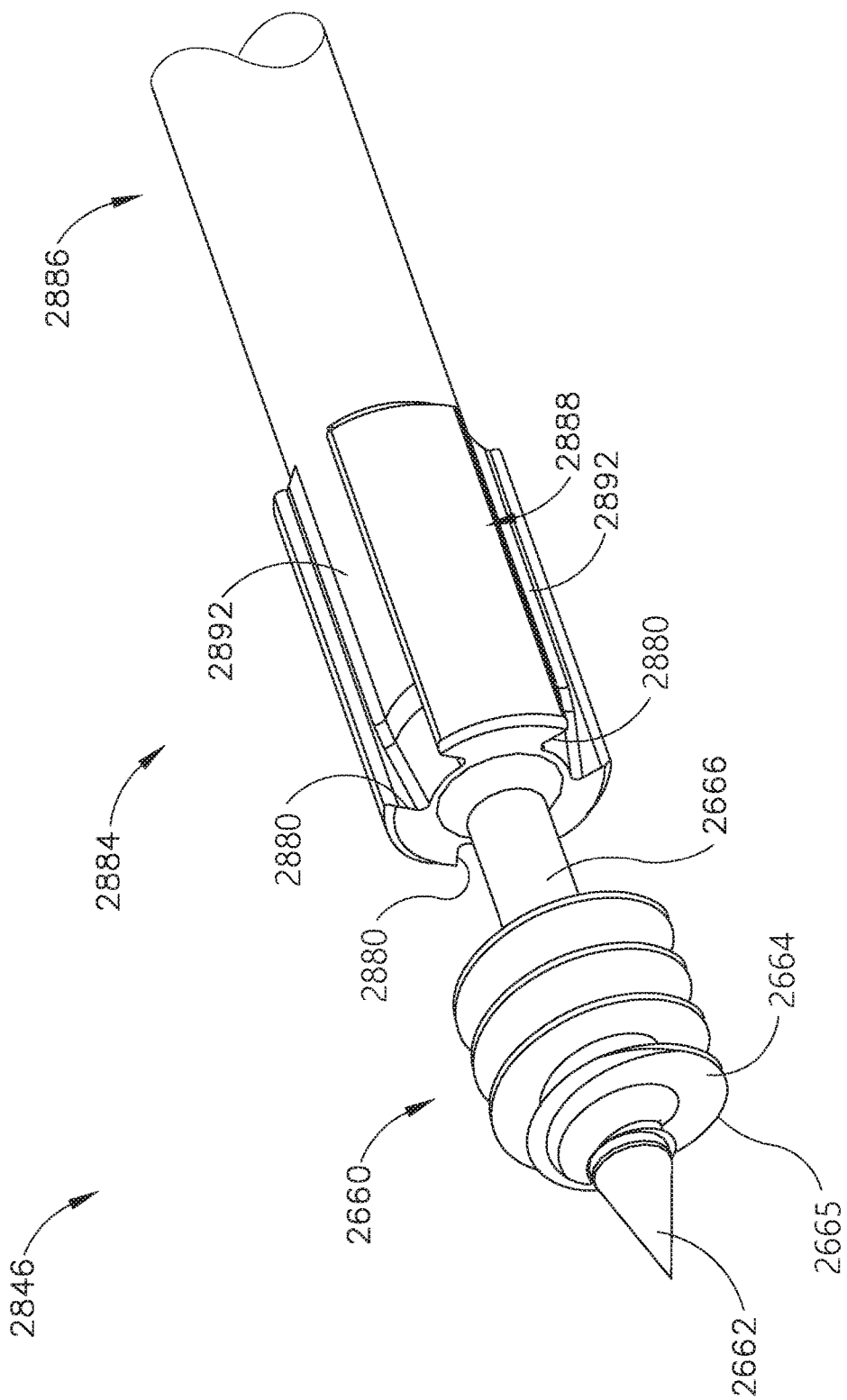
FIG. 17 depicts an enlarged perspective view of an exemplary auger of the shaft assembly of FIG. 16.

FIGS. 15-16 show the exemplary instrument (2800) that may be used to form an opening (FO) in a lamina wall in the sinus cavity such as the sinus wall (SW). The sinus wall (SW) may be a wall of the ethmoid bulla (EB) (e.g., the anterior face of the ethmoid bulla (EB)) or the wall of some other sinus cavity. The instrument (2800) of the present example comprises the handle assembly (2820) and the shaft assembly (2840). The handle assembly (2820) includes a first body portion (2822A) and a second body portion (2822B) coupled together to form a body (2822). The body (2822) defines a hole (2872) that receives a fluid tube (2874) extending through the body (2822).

A proximal end of the fluid tube (2874) includes an inlet (2875) that is configured to fluidly connect to a fluid supply (2876) for directing a fluid through the handle and shaft assemblies (2820, 2840) in order to discharge the fluid from the fluid passage (2870) and into the ethmoid bulla (EB). Alternatively, the proximal end of the fluid tube (2874) may be connected to a vacuum generator (2878) for communicating a vacuum to the fluid passage (2870) in order to suction the fluid and other debris. In some versions, the fluid is a saline solution and the fluid supply (2876) and the vacuum generator (2878) are each in the form of a conventional syringe (not shown) that is configured to contain the saline solution. In addition, the conventional syringe (not shown) may selectively connect to the inlet (2875) via a conventional luer fitting.

It will be appreciated that alternative fluids, fluid supplies, and vacuum generators may be used for irrigating and suctioning the ethmoid bulla (EB) or other sinus cavities. It should also be understood that two separate sources—a fluid supply (2876) and a vacuum generator (2878)—may be coupled with a single fluid tube (2874) via a Y-fitting or some other junction. Various suitable components and arrangements that may be used to provide fluid and/or suction through fluid tube (2874) will be apparent to those of ordinary skill in the art in view of the teachings herein. Regardless of the arrangement up to inlet (2875), the fluid passage (2870) extends from the inlet (2875) to at least one outlet (2880) positioned proximal to the helical flight (2664), such that the outlet (2880) fluidly communicates with the sinus cavity through the opening (FO) in the sinus wall (SW) as described in greater detail below.

The shaft assembly (2840) extends distally from the handle assembly (2820). As best seen in FIGS. 15-16, the shaft assembly (2640) comprises the outer sheath (2642), a cutter tube (2844) defining a lumen (2881) extending longitudinally therethrough, and a rotatable shaft (2846) received within the lumen (2881). As best seen in FIG. 16, a proximal end of the outer sheath (2642) is unitarily coupled with a distal portion of a sliding trigger (2630) such that longitudinal movement of the sliding trigger (2630) causes concurrent longitudinal sliding of the outer sheath (2642) along the longitudinal axis (LA1). The cutter tube (2844) is slidably disposed within the outer sheath (2642) such that the cutter tube (2844) and the outer sheath (2642) are able to translate independently relative to each other along the longitudinal axis (LA1).

Figure 20:
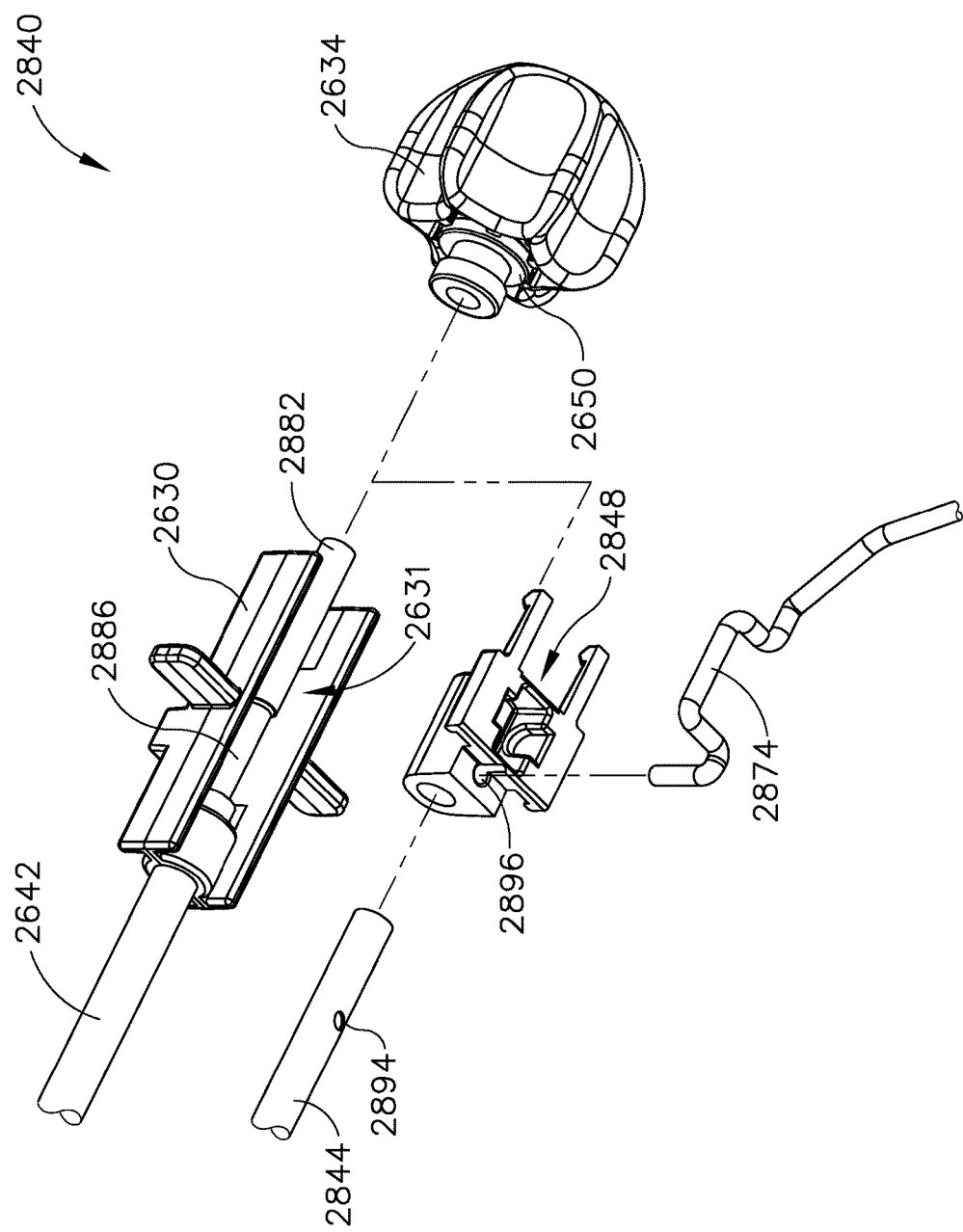
FIG. 20 depicts an enlarged exploded view of a proximal portion of the shaft assembly of FIG. 16.
Figure 21A:
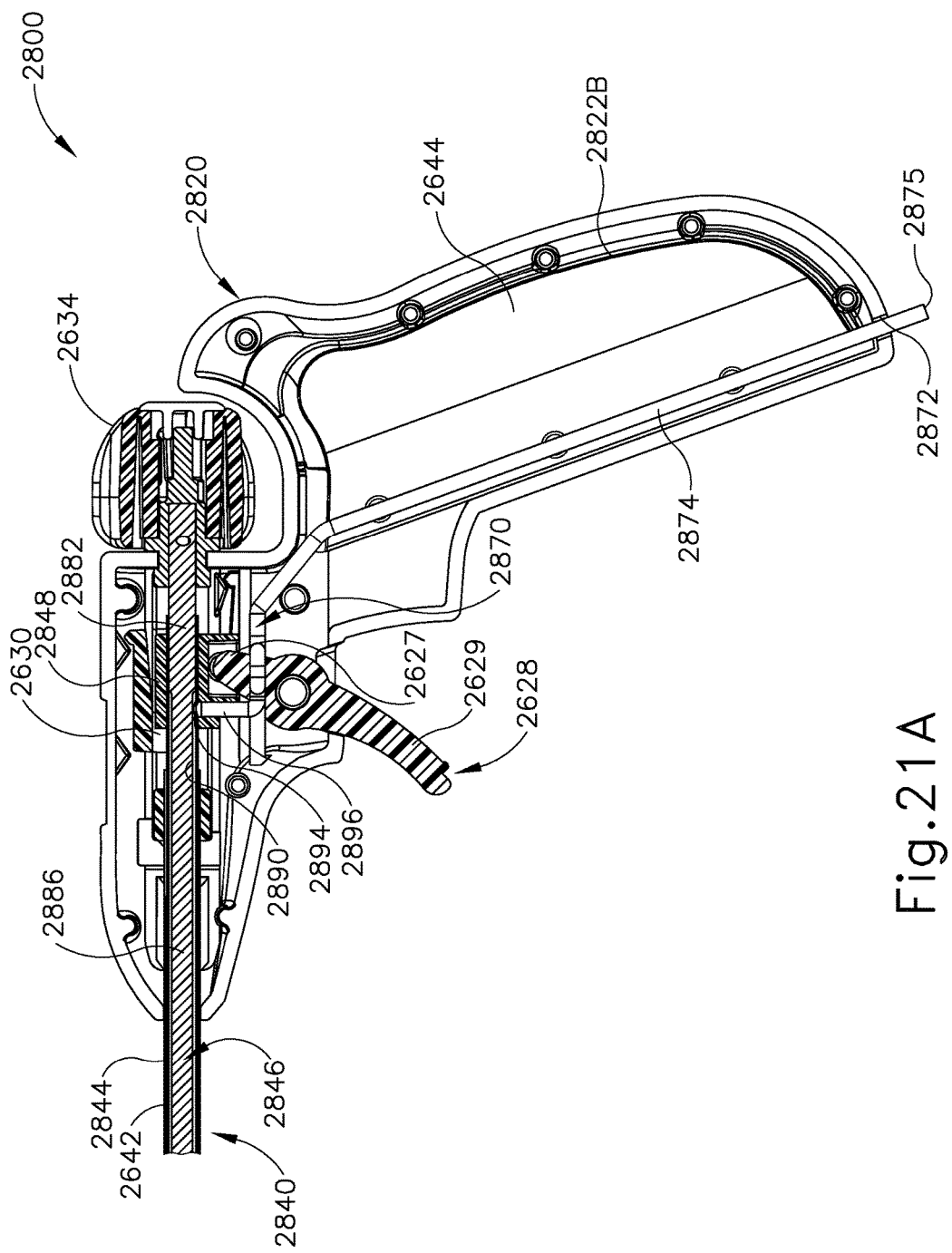
FIG. 21A depicts a cross-sectional view of a proximal portion of the instrument of FIG. 15 taken along section line 18-18 of FIG. 15, with a trigger of the handle assembly in a non-actuated position.
Figure 21B:
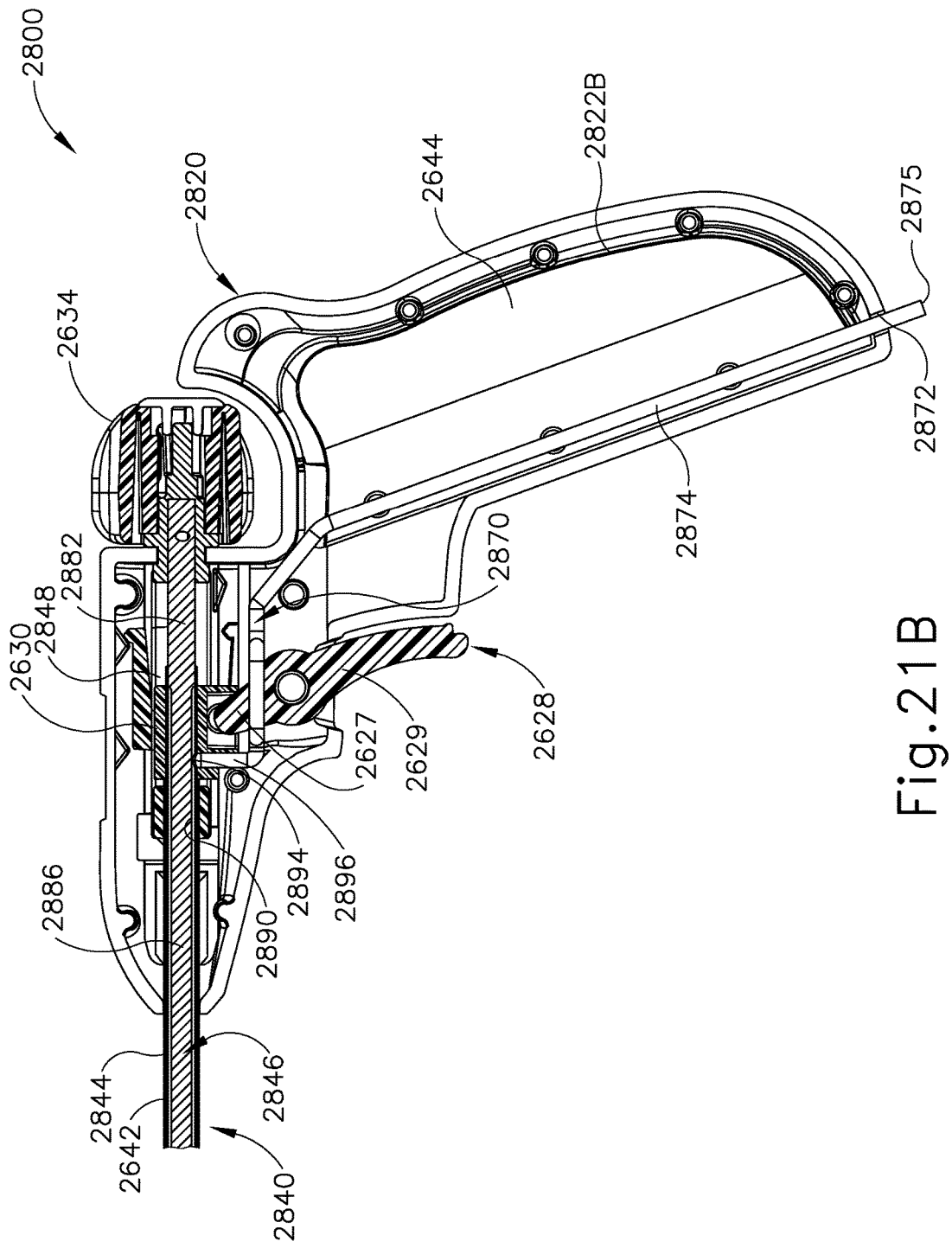
FIG. 21B depicts a cross-sectional view of a proximal portion of the instrument of FIG. 15 taken along section line 18-18 of FIG. 15, with a trigger of the handle assembly in an actuated position.
Figure 22:
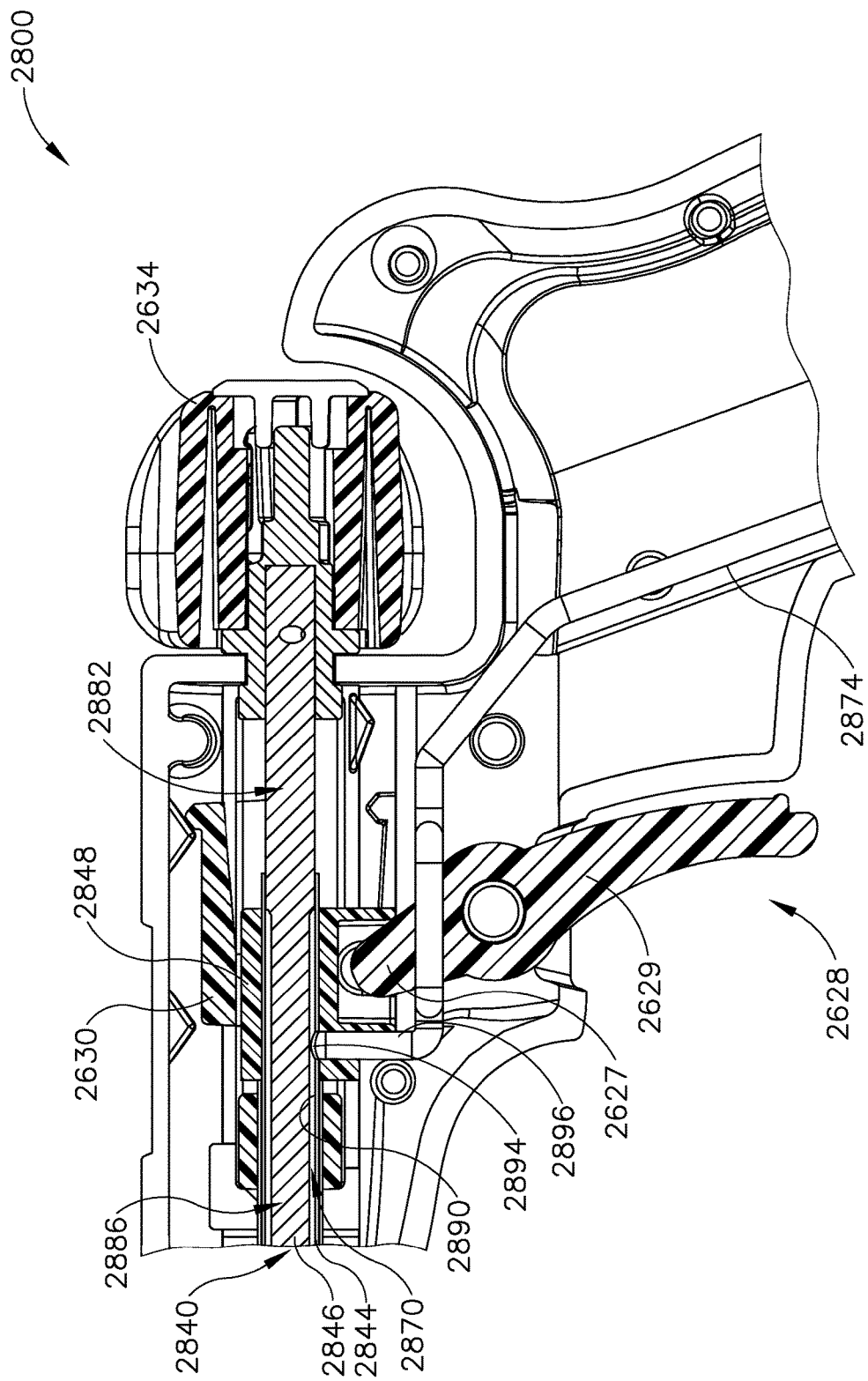
FIG. 22 depicts an enlarged cross-sectional view of the proximal portion of the instrument shown in FIG. 21B, with the trigger in the actuated position.

As best seen in FIG. 20, a proximal end of the cutter tube (2844) is integrally coupled with a sliding member (2848). The sliding member (2848) is slidably disposed within a proximal gap (2631) defined by the sliding trigger (2630) such that the sliding member (2848) slides longitudinally within the proximal gap (2631) of the sliding trigger (2630); and such that the sliding member (2848) and the sliding trigger (2630) are able to slide longitudinally independently relative to each other. As best seen in FIGS. 21A-22, the sliding member (2848) is pivotably coupled with the arm (2627) extending unitarily from the pivoting trigger (2628) in the opposite direction of the paddle (2629). An operator may thus advance the cutter tube (2844) distally relative to the handle assembly (2620) by squeezing the paddle (2629) toward the pistol grip (2624), as shown in the sequence depicted by FIGS. 21A-21B; then retract the cutter tube (2644) proximally by releasing the paddle (2629) as discussed above in greater detail.

As shown in FIG. 16, the rotatable shaft (2846) includes a proximal shaft end portion (2882), a distal shaft end portion (2884), and an intermediate shaft portion (2886) extending therebetween. As shown in FIGS. 16 and 22, the proximal shaft end portion (2882) is configured to connect to the rotatable knob (2634) so that the rotatable shaft (2846) may be rotated by the user, as discussed above in greater detail. The proximal shaft end portion (2882) also engages the cutter tube (2844) within the lumen (2881) to support the proximal shaft end portion (2882) within the cutter tube (2844). The distal shaft end portion (2884) includes the helical flight (2664) extending distally from the minor shaft (2666), also as discussed above in greater detail. However, according to the exemplary rotatable shaft (2846), the distal shaft end portion (2884) further includes a set of support bosses (2888) that are configured to support the rotatable shaft (2846) within the lumen (2881) while allowing shaft (2846) to rotate freely within cutter tube (2844).

Support bosses (2888) extend radially outwardly and are angularly spaced equidistantly from each other. Support bosses (2888) are positioned proximally adjacent to the minor shaft (2666). The intermediate shaft portion (2886) has a relatively smaller outer diameter than the proximal and distal shaft end portions (2882, 2884) such that the intermediate shaft portion (2886) is supported coaxially within the lumen (2881) between the proximal and distal shaft end portions (2882, 2884). Thereby, the intermediate shaft portion (2886) and the cutter tube (2844) collectively define an annular elongate gap or passage (2890) extending from the proximal shaft end portion (2882) to the distal shaft end portion (2884).

Figure 18:
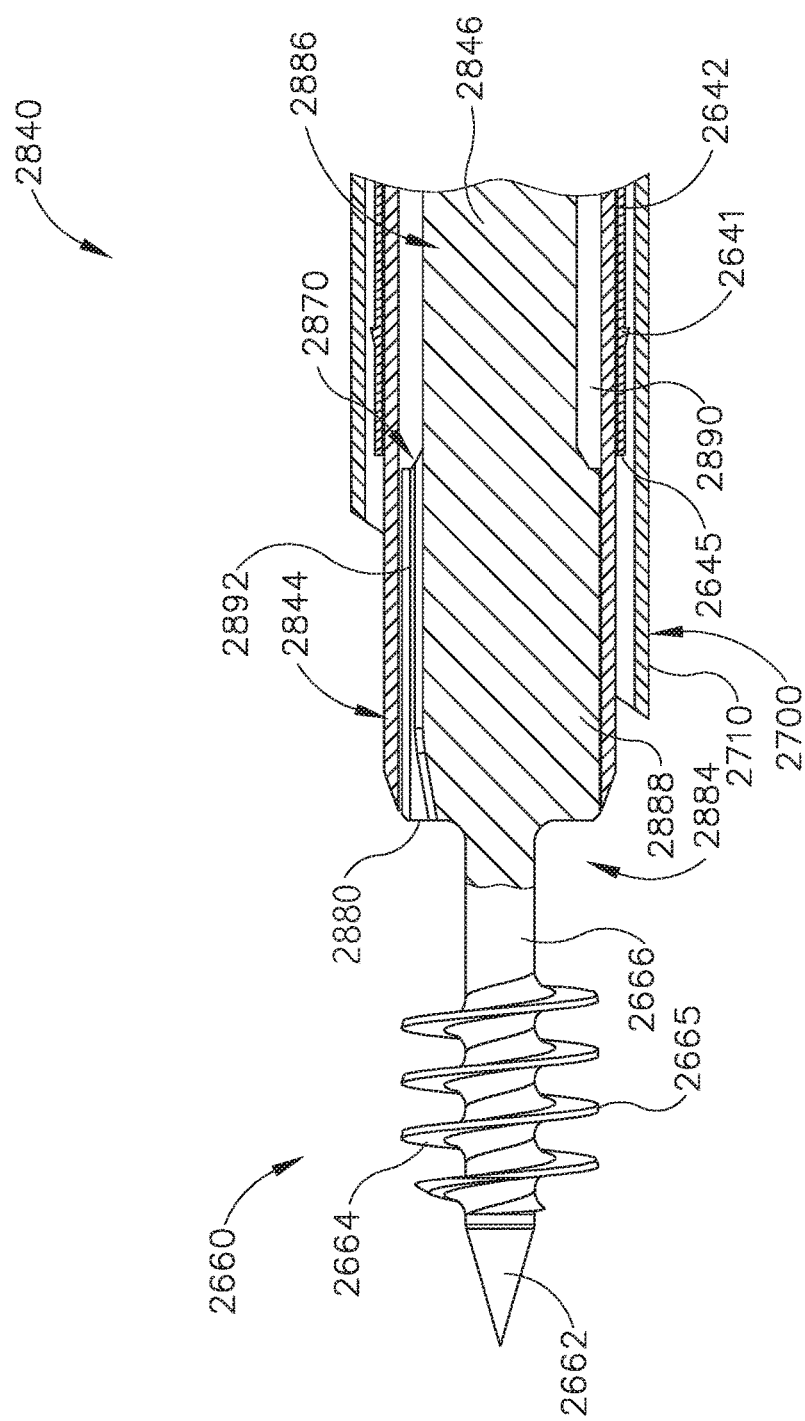
FIG. 18 depicts an enlarged cross-sectional view of a distal portion of the instrument of FIG. 15 taken along section line 18-18 of FIG. 15.
Figure 19:
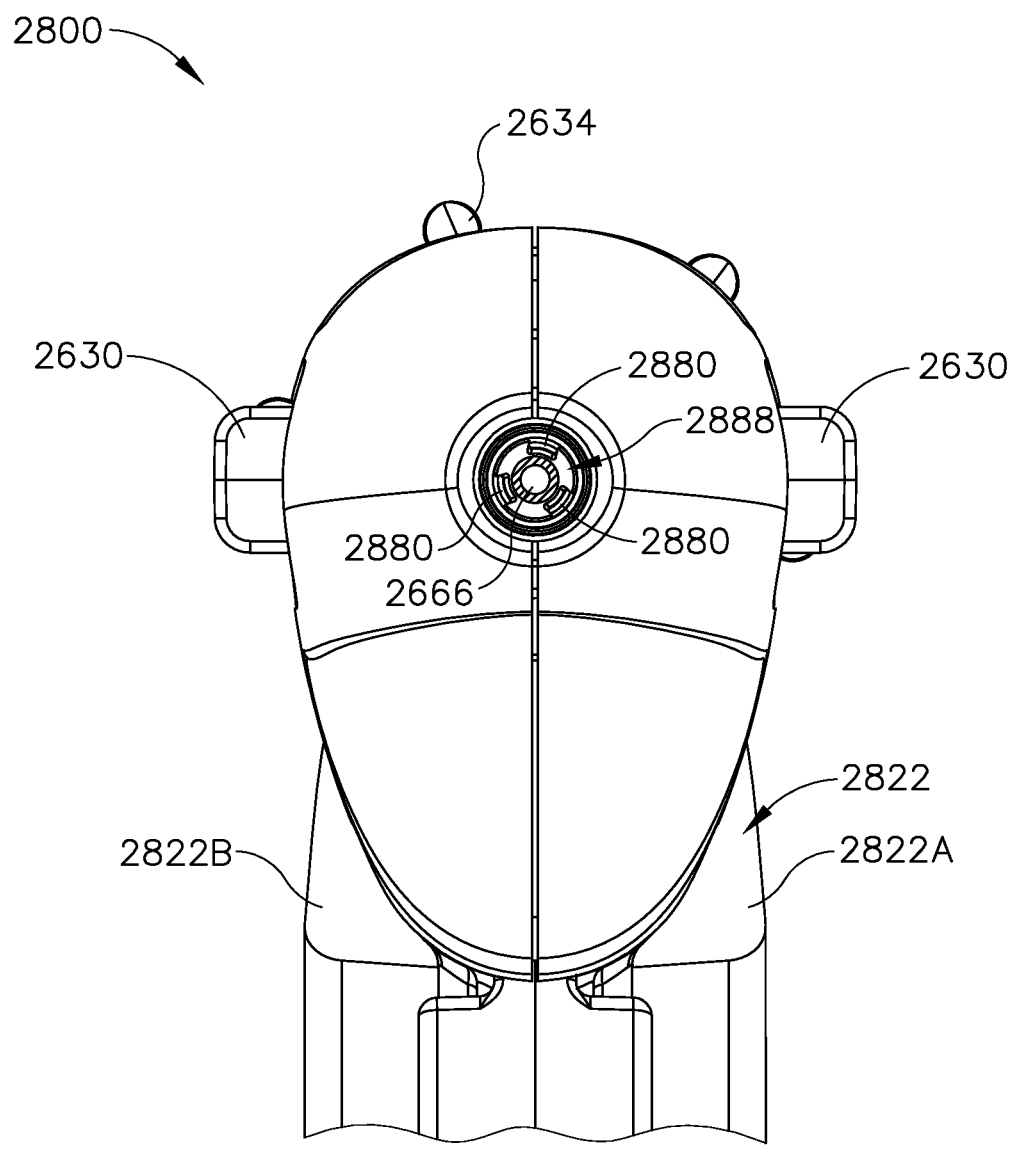
FIG. 19 depicts an enlarged cross-sectional view of the instrument of FIG. 15 taken along section line 19-19 of FIG. 15.

The annular elongate passage (2890) fluidly communicates with the outlet (2880) via a set of channels (2892) extending between the support bosses (2888). Specifically, the channels (2892) extend longitudinally along the support bosses (2888) between the outlet (2880) and the annular elongate passage (2892). As shown in FIGS. 18-19, the exemplary distal shaft end portion (2884) includes three outlets (2880) in fluid communication with the annular elongate passage (2892) via three respective channels (2892). The three outlets (2880) and three channels (2892) are equiangularly spaced about the support bosses (2888) to provide for the flow of fluid therethrough while simultaneously rotatably supporting the distal shaft end portion (2884) during use. In the present example, the outlets (2880), the channels (2892), and the annular elongate passage (2892) collectively define at least a portion of the fluid passage (2870) between the outer cutter tube (2844) and the inner rotatable shaft (2846). However, it will be appreciated that the fluid passage (2870), or any portion thereof, may be alternatively routed through the instrument (2800) to provide a path for communicating fluid from the inlet (2875) to the distal shaft end portion (2884). The invention is thus not intended to be unnecessarily limited to the exemplary configuration of the fluid passage (2870) described herein or shown in the drawings.

FIGS. 20-22 show the proximal portion of the shaft assembly (2840) in greater detail. The proximal end portion of the cutter tube (2844) includes a supply port (2894) in the form of a lateral opening, which is received within and secured to the sliding member (2848). In addition, the sliding member (2848) receives the fluid tube (2874) within a manifold passage (2896). The manifold passage (2896) extends from the fluid tube (2874) to the supply port (2894) in order to communicate fluid flowing through the instrument (2800) from the fluid tube (2874) to the annular elongate passage (2890), and vice versa. Proximal shaft end portion (2882) of rotatable shaft (2846) is also positioned within sliding member (2848). It should be understood that an o-ring, wiper seal, and/or some other feature may be positioned between the inner diameter of cutter tube (2844) and the outer diameter of proximal shaft portion (2882) in order to prevent irrigation fluid from escaping through the proximal end of sliding member (2848); and to prevent a loss of suction at the proximal end of sliding member (2848). Such a sealing member would be located proximal to supply port (2894) and would enable translation of cutter tube (2844) relative to rotatable shaft (2846); and further enable rotation of rotatable shaft (2846) relative to cutter tube (2844).

As shown in FIGS. 21A-21B, the fluid tube (2874) of the present example is generally flexible so as to accommodate movement of the sliding member (2848) and trigger (2628). As described herein, the term "flexible" may refer to any bending, flexing, and/or resiliency that may accommodate movement of the sliding member (2848). The fluid tube (2874) extends upwardly through the body (2822) from the hole (2872), routes distally around the trigger (2628), and is bent upwardly into fluid connection with the manifold passage (2896). When the user selectively actuates the trigger (2628), the fluid tube (2874) flexes to accommodate like movement of the sliding member (2848) as shown in FIG. 21B. The fluid tube (2874) will similarly accommodate return movement of the sliding member (2848).

FIG. 22 shows an enlarged view of the proximal portion of the shaft assembly (2840) that more clearly shows the fluid passage (2870) through the body (2822). The exemplary fluid passage (2870) is further defined by the fluid tube (2874), the manifold passage (2896), and the supply port (2894) into the annular elongate passage (2890). However, as discussed above, it will be appreciated that the fluid passage (2870), or any portion thereof, may be alternatively routed through the instrument (2800) to provide a path for communicating fluid through the instrument (2800).

Figure 23A:
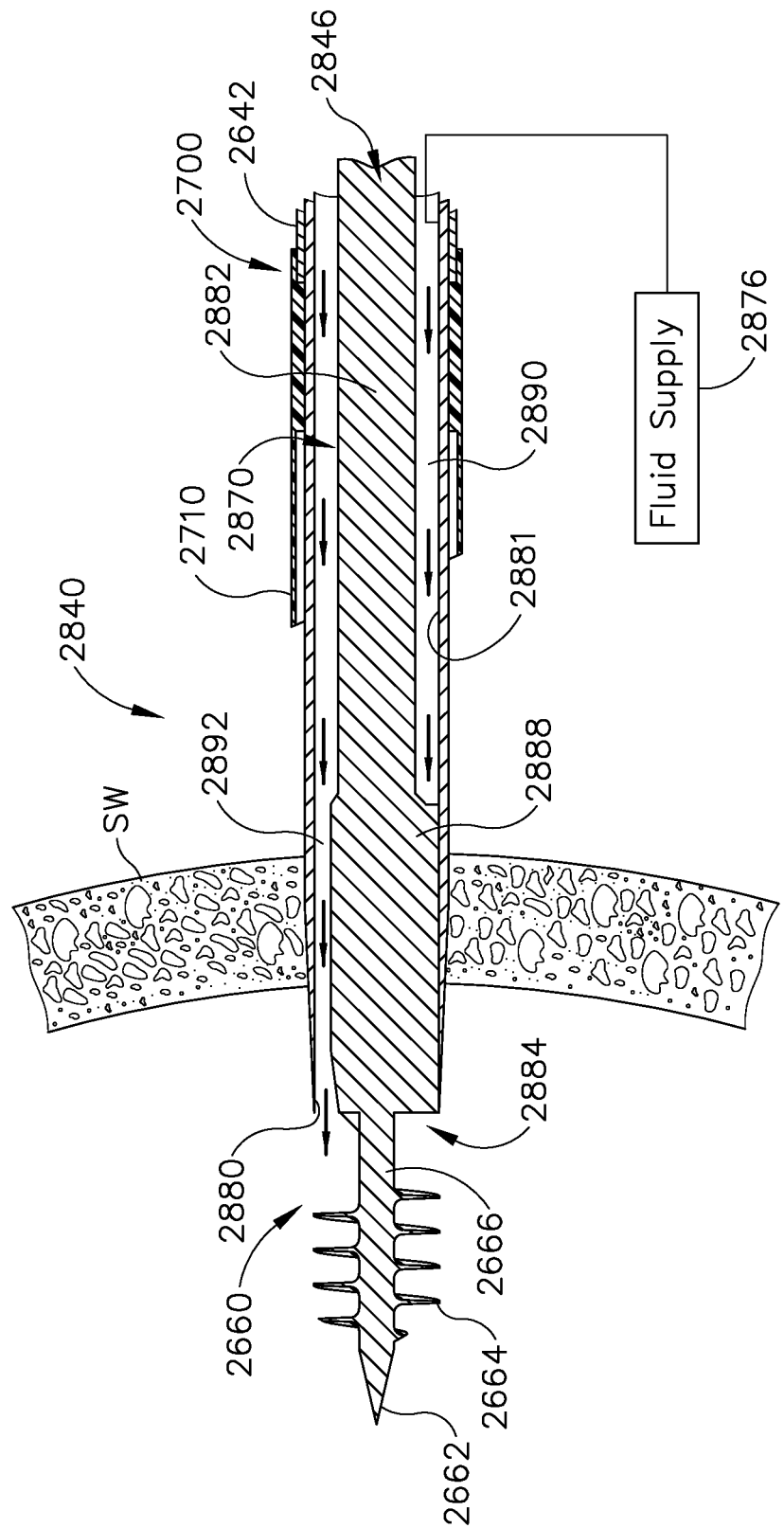
FIG. 23A depicts a side cross-sectional view of the shaft assembly of FIG. 15, with a cutter advanced distally and discharging an irrigation fluid while a remainder of the shaft assembly remains in the third longitudinal position.
Figure 23B:
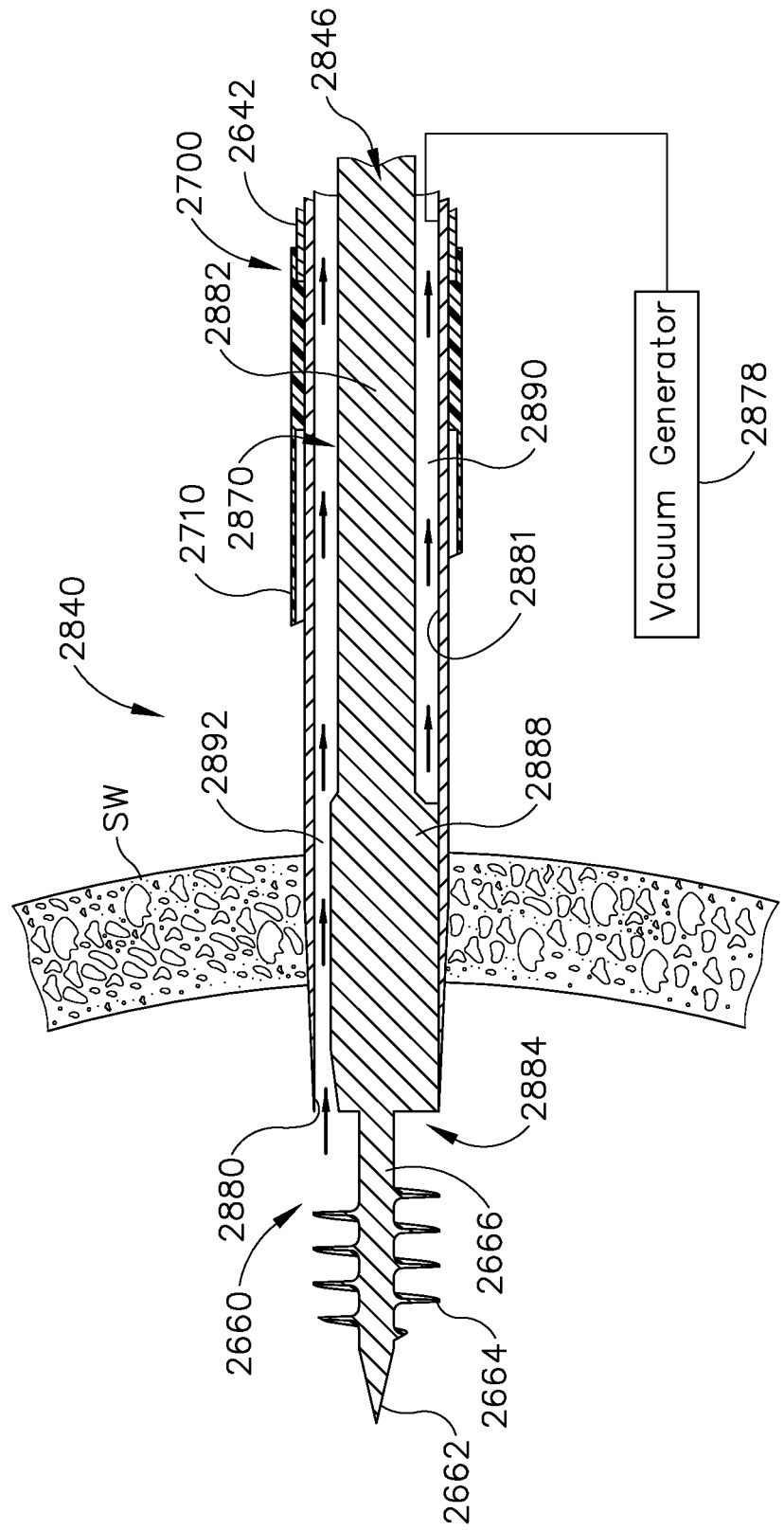
FIG. 23B depicts a side cross-sectional view of the shaft assembly of FIG. 15, with a cutter advanced distally and applying suction while a remainder of the shaft assembly remains in the third longitudinal position.

In use, the cutter tube (2844) and the rotatable shaft (2846) are configured to form the opening through the sinus wall (SW) as discussed above for treating the sinus cavity and as shown in FIGS. 23A-23B. In addition, the instrument (2800) is configured to irrigate the sinus cavity with the fluid and then, with the same instrument (2800), suction the fluid, and any included debris, from the sinus cavity prior to removal of the instrument.

To this end, after the cutter tube (2844) cuts through the sinus wall (SW), the rotatable shaft (2846) may be advanced distally beyond the cutter tube (2844) such that the outlets (2880) are in direct fluid communication with the sinus cavity. Various suitable ways in which rotatable shaft (2846) may be advanced distally will be apparent to those of ordinary skill in the art in view of the teachings herein. Alternatively, cutter tube (2844) and outer sheath (2642) may be retracted relative to rotatable shaft (2846) to reach the arrangement shown in FIG. 23A. It should also be understood that, in some instances, the rotatable shaft (2846) may remain covered by the cutter tube (2844) and still fluidly communicate with the sinus cavity through the cutter tube (2844). In order to irrigate the sinus cavity, a pressurized fluid (e.g., saline, etc.) from a fluid supply (2876), such as a syringe (not shown), is forced through the fluid passage (2870). The fluid then discharges from the outlets, as shown in FIG. 23A, in order to loosen debris within the sinus cavity.

The user may also suction the fluid and associated debris from the sinus cavity by disconnecting the fluid supply (2876) from the inlet (2875) and then connecting the vacuum generator (2878) to the inlet (2875) as shown in FIG. 23B. Alternatively, the user may generate the vacuum by simply withdrawing the plunger (not shown) from the syringe (not shown) already connected to the inlet (2875). As yet another merely illustrative example, the user may actuate a valve to transition the input to inlet (2875) from a fluid supply (2876) to a vacuum generator (2878). In any case, the fluid passage (2870) communicates the vacuum to the outlets (2880) to suction the fluid and associated debris from the sinus cavity. Thereby, the user may form the opening (FO) and immediately thereafter irrigate the sinus cavity and suction the sinus cavity with only a single insertion of the instrument (2800) into the patient without further removal until the opening (FO) formation, irrigation, and suction are compltete. Once suctioned, the entire shaft assembly (2820) is retracted proximally to reveal the formed opening (FO) in the sinus wall (SW), as shown in FIG. 14F.

While the shaft assembly (2840) is described above as being used in a ethmoidotomy procedure, it should be understood that the shaft assembly (2840) may also be used in other kinds of procedures within a patient. Other suitable procedures in which the shaft assembly (2840) may be used will be apparent to those of ordinary skill in the art in view of the teachings herein. In addition, it will be further appreciated that the treatment may not require successive steps of forming the opening, irrigating the sinus cavity, and suctioning the sinus cavity, respectively, in each instance of treatment. Rather, the treatment may include any number of these steps in any order understood to be appropriate by the user. For example, one exemplary treatment may only include irrigating the sinus cavity, whereas another exemplary treatment may only include suctioning the sinus cavity. The method of using the shaft assembly (2840) is thus not limited to the successive order of treatment described herein.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An instrument, comprising: (a) a cutter member having a lumen longitudinally extending therethrough; (b) a rotatable member having a distal end portion and extending through the lumen within the cutter member, the rotatable member having a helical blade projecting from the distal end portion, wherein the cutter member is operable to translate relative to the rotatable member to selectively cover at least a portion of the helical blade and form an opening into a sinus cavity; and (c) a fluid passage defined by at least one of the cutter member and the rotatable member, the fluid passage extending through the cutter member from an inlet to a first outlet, the first outlet positioned proximal to the helical blade such that the first outlet is configured to fluidly communicate with a sinus cavity via the opening, wherein the inlet is configured to receive at least one of a fluid and a vacuum in order to communicate the at least one of the fluid and the vacuum to the first outlet and introduce the at least one of the fluid and the vacuum into the sinus cavity for irrigating the sinus cavity or suctioning the sinus cavity, respectively.

Example 2

The instrument of Example 1, wherein the fluid passage is defined between the rotatable member and the cutter member.

Example 3

The instrument of Example 2, further comprising a first channel extending longitudinally along the rotatable member from the first outlet toward the inlet, wherein the first channel further defines the fluid passage.

Example 4

The instrument of Example 3, wherein the fluid passage further includes a second outlet and a third outlet, each of the second and third outlets being positioned proximal to the helical blade such that the second and third outlet are configured to fluidly communicate with the sinus cavity via the opening, the instrument further comprising: (a) a second channel extending longitudinally along the rotatable member from the second outlet toward the inlet, wherein the second channel further defines the fluid passage; and (b) a third channel extending longitudinally along the rotatable member from the third outlet toward the inlet, wherein the third channel further defines the fluid passage, wherein the first, second, and third channels are equiangularly spaced about the rotatable member.

Example 5

The instrument of any one or more of Examples 1 through 4, wherein the rotatable member further includes: (i) a proximal end portion opposite the distal end portion, (ii) an intermediate portion positioned between the proximal and distal end portions, the intermediate portion and the cutter member collectively defining an elongate passage therebetween, the elongate passage further defining the fluid passage, and (iii) a support boss extending at least partially around the distal end portion of the rotatable member, wherein the support boss is positioned against the cutter member within the lumen and supports the intermediate portion of the rotatable member projecting proximally therefrom within the lumen.

Example 6

The instrument of Example 5, further comprising a first channel extending longitudinally through the support boss between the first outlet and the elongate passage, wherein the first channel further defines the fluid passage for fluid communication therethrough.

Example 7

The instrument of Example 6, wherein the fluid passage further includes a second outlet and a third outlet, each of the second and third outlets being positioned proximal to the helical blade such that the second and third outlet are configured to fluidly communicate with the sinus cavity via the opening, wherein the instrument further comprises: (a) a second channel extending longitudinally through the support boss between the second outlet and the elongate passage, wherein the second channel further defines the fluid passage for fluid communication therethrough; and (b) a third channel extending longitudinally through the support boss between the third outlet and the elongate passage, wherein the third channel further defines the fluid passage for fluid communication therethrough, wherein the first, second, and third channels are equiangularly spaced about the support boss.

Example 8

The instrument of any one or more of Examples 1 through 7, further comprising a sliding member configured to selectively translate longitudinally, wherein the sliding member is coupled to the cutter member to direct longitudinal movement of the cutter member relative to the rotatable member.

Example 9

The instrument of Example 8, further comprising an elongate passage defined by at least one of the rotatable member and the cutting tube, wherein the elongate passage is fluidly connected to the first outlet and further defines the fluid passage, wherein the sliding member includes a manifold passage extending therethrough, wherein the manifold passage is fluidly connected to the elongate passage and is configured to receive at least one of the fluid and the vacuum in order to communicate the at least one of the fluid and the vacuum from the manifold passage to the elongate passage.

Example 10

The instrument of Example 9, further comprising a supply tube coupled with the sliding member and fluidly connected to the manifold passage, the supply tube having the inlet opposite the sliding member such that the inlet is configured to connect to at least one of the fluid supply and the vacuum generator for receiving at least one of the fluid and the vacuum, respectively.

Example 11

The instrument of Example 10, wherein the supply tube comprises a flexible supply tube such that the flexible supply tube is configured to flexibly move with the sliding member.

Example 12

The instrument of claim 9, wherein the cutter member further includes a lateral fluid bore, the lateral fluid bore extending from the lumen to the manifold passage within the sliding member such that the manifold passage is in fluid communication with the elongate passage.

Example 13

The instrument of any one or more of Examples 1 through 12, wherein the rotatable member has a pointed distal tip.

Example 14

The instrument of any one or more of Examples 1 through 13, further comprising a handle assembly operatively connected to the rotatable member and the cutter member, the handle assembly configured to be gripped by a user and support the rotatable member and the cutter member during treatment of the patient.

Example 15

The instrument of any one or more of Examples 1 through 14, further comprising at least one of a fluid supply and a vacuum generator, wherein the at least one of the fluid supply and the vacuum generator is in the form of a syringe configured to fluidly connect to the fluid passage.

Example 16

An instrument, comprising: (a) a cutter member having a lumen longitudinally extending therethrough; (b) a rotatable member having a distal end portion and extending through the lumen within the cutter member, the rotatable member having a helical blade projecting from the distal end portion, wherein the cutter member is operable to translate relative to the rotatable member to selectively cover at least a portion of the helical blade and form an opening into a sinus cavity; (c) a sliding member configured to selectively translate longitudinally, wherein the sliding member is coupled to the cutter member to direct longitudinal movement of the cutter member relative to the rotatable member; and (c) a fluid passage defined between the cutter member and the rotatable member, the fluid passage extending through the cutter member from an inlet to a first outlet, wherein the first outlet is positioned proximal to the helical blade such that the first outlet is configured to fluidly communicate with the sinus cavity via the opening, wherein the rotatable member further includes: (i) a proximal end portion opposite the distal end portion, (ii) an intermediate portion positioned between the proximal and distal end portions, the intermediate portion and the cutter member collectively defining an elongate passage therebetween, the elongate passage further defining the fluid passage, and (iii) a support boss extending at least partially around the distal end portion of the rotatable member, wherein the support boss is positioned against the cutter member within the lumen and supports the intermediate portion of the rotatable member projecting proximally therefrom within the lumen, wherein the inlet is configured to receive at least one of a fluid and a vacuum in order to communicate the at least one of the fluid and the vacuum to the first outlet and introduce the at least one of the fluid and the vacuum into the sinus cavity for irrigating the sinus cavity or suctioning the sinus cavity, respectively.

Example 17

A method of treating a sinus cavity, comprising: (a) forming an opening in a sinus wall with a distal end portion of an instrument; and (b) treating the sinus cavity by at least one of irrigating and suctioning the sinus cavity with the distal end portion of the instrument.

Example 18

The method of Example 17, wherein forming the opening further comprises: (a) piercing the sinus wall by driving a rotating member of the distal end portion through the sinus wall, wherein the rotating member includes a helical flight; and (b) driving a cutter member of the distal end portion distally over the rotating member and through the sinus wall, wherein the rotating member is held stationary relative to the sinus wall during the act of driving the cutter member distally, wherein the act of driving the cutter member through the sinus wall forms the opening in the sinus wall.

Example 19

The method of Example 18, wherein the distal end portion of the instrument includes an outlet fluidly connected to a fluid source, wherein the first outlet is positioned proximal to the helical flight, wherein treating the sinus cavity further comprises discharging a fluid from the outlet and into the sinus cavity in order to irrigate the sinus cavity.

Example 20

The method of any one or more of Examples 18 through 19, wherein the distal end portion of the instrument includes an outlet fluidly connected to vacuum generator, wherein the first outlet is positioned proximal to the helical flight, wherein treating the sinus cavity further comprises generating a vacuum at the outlet positioned within the sinus cavity in order to suction a fluid from the sinus cavity.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An instrument, comprising:
   (a) a handle assembly configured to be gripped by a user, wherein the handle assembly includes first and second opposing lateral slots;
   (b) an outer sheath having a first lumen longitudinally extending therethrough;
   (c) a cutter member having a second lumen longitudinally extending therethrough, wherein the cutter member is slidably disposed within the first lumen such that the cutter member is configured to translate independently relative to the outer sheath;
   (d) a rotatable member having a distal end portion and extending through the second lumen within the cutter member, the rotatable member having a helical blade projecting from the distal end portion;
   (e) a first trigger configured to simultaneously translate the cutter member relative to both the outer sheath and the helical blade of the rotatable member to selectively cover at least a portion of the helical blade and form an opening into a sinus cavity of a patient;
   (f) a fluid passage defined by at least one of the cutter member and the rotatable member, the fluid passage extending through the cutter member from an inlet to a first outlet, the first outlet positioned proximal to the helical blade such that the first outlet is configured to fluidly communicate with the sinus cavity via the opening; and
   (g) a second trigger operatively coupled with the outer sheath, wherein the second trigger is configured to selectively longitudinally translate causing the outer sheath to longitudinally translate relative to the helical blade of the rotatable member while the rotatable member is located within the patient, wherein the second trigger includes first and second projecting portions that extend laterally from the respective first and second opposing lateral slots, wherein the first and second projecting portions are configured to be selectively longitudinally movable by the user, wherein the inlet is configured to receive at least one of a fluid and a vacuum in order to communicate the at least one of the fluid and the vacuum to the first outlet and introduce the at least one of the fluid and the vacuum into the sinus cavity for irrigating the sinus cavity or suctioning the sinus cavity, respectively.

2. The instrument of claim 1, wherein the fluid passage is defined between the rotatable member and the cutter member.

3. The instrument of claim 2, further comprising a first channel extending longitudinally along the rotatable member from the first outlet toward the inlet, wherein the first channel further defines the fluid passage.

4. The instrument of claim 3, wherein the fluid passage further includes a second outlet and a third outlet, each of the second and third outlets being positioned proximal to the helical blade such that the second and third outlet are configured to fluidly communicate with the sinus cavity via the opening, the instrument further comprising:
   (a) a second channel extending longitudinally along the rotatable member from the second outlet toward the inlet, wherein the second channel further defines the fluid passage; and
   (b) a third channel extending longitudinally along the rotatable member from the third outlet toward the inlet, wherein the third channel further defines the fluid passage,
   wherein the first, second, and third channels are equiangularly spaced about the rotatable member.

5. The instrument of claim 1, wherein the rotatable member further includes:
   (i) a proximal end portion opposite the distal end portion,
   (ii) an intermediate portion positioned between the proximal and distal end portions, the intermediate portion and the cutter member collectively defining an elongate passage therebetween, the elongate passage further defining the fluid passage, and
   (iii) a support boss extending at least partially around the distal end portion of the rotatable member, wherein the support boss is positioned against the cutter member within the second lumen and supports the intermediate portion of the rotatable member projecting proximally therefrom within the second lumen.

6. The instrument of claim 5, further comprising a first channel extending longitudinally through the support boss between the first outlet and the elongate passage, wherein the first channel further defines the fluid passage for fluid communication therethrough.

7. The instrument of claim 6, wherein the fluid passage further includes a second outlet and a third outlet, each of the second and third outlets being positioned proximal to the helical blade such that the second and third outlet are configured to fluidly communicate with the sinus cavity via the opening, wherein the instrument further comprises:
   (a) a second channel extending longitudinally through the support boss between the second outlet and the elongate passage, wherein the second channel further defines the fluid passage for fluid communication therethrough; and
   (b) a third channel extending longitudinally through the support boss between the third outlet and the elongate passage, wherein the third channel further defines the fluid passage for fluid communication therethrough,
   wherein the first, second, and third channels are equiangularly spaced about the support boss.

8. The instrument of claim 1, further comprising a sliding member configured to selectively translate longitudinally, wherein the sliding member is coupled to the cutter member to direct longitudinal movement of the cutter member relative to the rotatable member.

9. The instrument of claim 8, further comprising an elongate passage defined by at least one of the rotatable member and the cutter member, wherein the elongate passage is fluidly connected to the first outlet and further defines the fluid passage, wherein the sliding member includes a manifold passage extending therethrough, wherein the manifold passage is fluidly connected to the elongate passage and is configured to receive the at least one of the fluid and the vacuum in order to communicate the at least one of the fluid and the vacuum from the manifold passage to the elongate passage.

10. The instrument of claim 9, further comprising a supply tube coupled with the sliding member and fluidly connected to the manifold passage, the supply tube having the inlet opposite the sliding member such that the inlet is configured to connect to at least one of a fluid supply and a vacuum generator for receiving the at least one of the fluid and the vacuum, respectively.

11. The instrument of claim 9, wherein the cutter member further includes a lateral fluid bore, the lateral fluid bore extending from the second lumen to the manifold passage within the sliding member such that the manifold passage is in fluid communication with the elongate passage.

12. The instrument of claim 1, further comprising at least one of a fluid supply and a vacuum generator, wherein the at least one of the fluid supply and the vacuum generator is in the form of a syringe configured to fluidly connect to the fluid passage.

13. The instrument of claim 1, wherein the cutter member is operable to translate relative to both the outer sheath and the rotatable member to selectively cover the portion of the helical blade and form the opening into the sinus cavity of the patient.

14. An instrument, comprising:
(a) a handle assembly, wherein the handle assembly includes at least one slot;
(b) a cutter member having a lumen longitudinally extending therethrough;
(c) a rotatable member having a distal end portion and extending through the lumen within the cutter member, the rotatable member having a helical blade projecting from the distal end portion;
(d) an outer sheath having an outer sheath lumen, wherein the outer sheath lumen is configured to receive the cutter member;
(e) a first trigger configured to simultaneously translate the cutter member relative to both the outer sheath and the helical blade of the rotatable member to selectively cover at least a portion of the helical blade and form an opening into a sinus cavity of a patient;
(f) a second trigger operatively coupled with the outer sheath, wherein the second trigger is configured to selectively longitudinally translate within the at least one slot of the handle assembly causing the outer sheath to longitudinally translate relative to the helical blade of the rotatable member when the rotatable member is located within the patient; and
(g) a fluid passage defined by at least one of the cutter member and the rotatable member, the fluid passage extending through the cutter member from an inlet to a first outlet, the first outlet positioned proximal to the helical blade such that the first outlet is configured to fluidly communicate with the sinus cavity via the opening,
wherein the inlet is configured to receive at least one of a fluid and a vacuum in order to communicate the at least one of the fluid and the vacuum to the first outlet and introduce the at least one of the fluid and the vacuum into the sinus cavity for irrigating the sinus cavity or suctioning the sinus cavity, respectively.

15. The instrument of claim 14, further comprising a first channel extending longitudinally along the rotatable member from the first outlet toward the inlet, wherein the first channel further defines the fluid passage, wherein the fluid passage further includes a second outlet and a third outlet, each of the second and third outlets being positioned proximal to the helical blade such that the second and third outlet are configured to fluidly communicate with the sinus cavity via the opening, the instrument further comprising:
(a) a second channel extending longitudinally along the rotatable member from the second outlet toward the inlet, wherein the second channel further defines the fluid passage; and
(b) a third channel extending longitudinally along the rotatable member from the third outlet toward the inlet, wherein the third channel further defines the fluid passage,
wherein the first, second, and third channels are equiangularly spaced about the rotatable member.

16. The instrument of claim 14, wherein the handle assembly includes a pistol grip configured to be grasped by a user, wherein the first trigger is pivotable toward and away from the pistol grip.

17. An instrument, comprising:
(a) an outer sheath having a first lumen longitudinally extending therethrough;
(b) a cutter member having a second lumen longitudinally extending therethrough, wherein the cutter member is slidably disposed within the first lumen such that the cutter member is configured to translate independently relative to the outer sheath, wherein the cutter member includes a lateral fluid bore;
(c) a rotatable member having a distal end portion and extending through the second lumen within the cutter member, the rotatable member having a helical blade projecting from the distal end portion;
(d) a first trigger configured to simultaneously translate the cutter member relative to both the outer sheath and the helical blade of the rotatable member to selectively cover at least a portion of the helical blade and form an opening into a sinus cavity of a patient;
(e) a sliding member configured to selectively translate longitudinally, wherein the sliding member is coupled to the cutter member to direct longitudinal movement of the cutter member relative to the rotatable member;
(f) a fluid passage defined by at least one of the cutter member and the rotatable member, wherein the fluid passage extends through the cutter member from an inlet to a first outlet, wherein the inlet is configured to receive at least one of a fluid and a vacuum in order to communicate the at least one of the fluid and the vacuum to the first outlet and introduce the at least one of the fluid and the vacuum into the sinus cavity for irrigating the sinus cavity or suctioning the sinus cavity, respectively, wherein the first outlet is positioned proximal to the helical blade such that the first outlet is configured to fluidly communicate with the sinus cavity via the opening;
(g) an elongate passage defined by at least one of the rotatable member and the cutter member, wherein the elongate passage is fluidly connected to the first outlet and further defines the fluid passage, wherein the sliding member includes a manifold passage extending therethrough, wherein the manifold passage is fluidly connected to the elongate passage and is configured to receive the at least one of the fluid and the vacuum in order to communicate the at least one of the fluid and the vacuum from the manifold passage to the elongate passage, wherein the lateral fluid bore extends from the second lumen to the manifold passage within the sliding member such that the manifold passage is in fluid communication with the elongate passage; and (h) a second trigger operatively coupled with the outer sheath, wherein the second trigger is configured to selectively longitudinally translate causing the outer sheath to longitudinally translate relative to the helical blade of the rotatable member while the rotatable member is located within the patient.

* * * * *